(12) United States Patent
Spierer et al.

(10) Patent No.: US 11,837,107 B2
(45) Date of Patent: Dec. 5, 2023

(54) TECHNIQUE FOR CONTROLLING A HUMAN MACHINE INTERFACE

(71) Applicant: UNIVERSITÉ DE FRIBOURG, Fribourg (CH)

(72) Inventors: Lucas Spierer, Lausanne (CH); Maurizio Rigamonti, Villars-sur-Glâne (CH); Hugo Najberg, Bourguillon (CH)

(73) Assignee: UNIVERSITÉ DE FRIBOURG, Fribourg (CH)

( * ) Notice: Subject to any disclaimer, the term of this patent is extended or adjusted under 35 U.S.C. 154(b) by 194 days.

(21) Appl. No.: 17/525,732

(22) Filed: Nov. 12, 2021

(65) Prior Publication Data
US 2022/0157191 A1   May 19, 2022

(30) Foreign Application Priority Data
Nov. 13, 2020 (EP) .................................... 20207380

(51) Int. Cl.
G06F 11/34 (2006.01)
G09B 19/00 (2006.01)

(52) U.S. Cl.
CPC .......... *G09B 19/00* (2013.01); *G06F 11/3428* (2013.01); *G06F 11/3438* (2013.01)

(58) Field of Classification Search
CPC ...................................................... G06F 11/34
See application file for complete search history.

(56) References Cited

U.S. PATENT DOCUMENTS

| 9,349,297 | B1* | 5/2016 | Ortiz | G06V 10/761 |
| 9,881,515 | B2 | 1/2018 | Moreno | |
| 2016/0163037 | A1* | 6/2016 | Dehais | G06T 7/521 382/110 |
| 2017/0098385 | A1 | 4/2017 | Martucci et al. | |
| 2019/0213416 | A1* | 7/2019 | Cho | G06V 20/20 |

FOREIGN PATENT DOCUMENTS

WO   2018132483 A1   7/2018

OTHER PUBLICATIONS

Jens Blechert et al. In "Food-pics: an image database for experimental research on eating and appetite," Front. Psychol., vol. 5, p. 617, Jun. 2014, doi: 10.3389/fpsyg.2014.00617.

(Continued)

*Primary Examiner* — Di Xiao
(74) *Attorney, Agent, or Firm* — Ewers IP Law PLLC; Falk Ewers

(57) ABSTRACT

A technique for controlling a human machine interface is provided. A first task includes outputting a predefined criterion applicable to each of a plurality of physical objects. Each object is associated with a category within a group of at least pairwise disjoint categories with the criterion fulfilled for each object in a first category and not fulfilled for each object in a second category. Controlling the HMI for the first task includes repeatedly performing the steps of rendering an object; monitoring the HMI for an input during a predefined first time period after the rendering of the object; and updating a first metric indicative of a performance measurement in the first task. The method further comprises rendering a plurality of receptacles each enclosing one of the objects for a second task.

15 Claims, 13 Drawing Sheets

(56) References Cited

OTHER PUBLICATIONS

Harm Veling et al. "What Is Trained During Food Go/No-Go Training? A Review Focusing on Mechanisms and a Research Agenda", in Curr. Addict. Rep., vol. 4, No. 1, pp. 35-41 (2017).
Naomi Kakoschke et al. "Approach bias modification training and consumption: A review of the literature",in Addictive Behaviors., vol. 64, pp. 21-28, (Jan. 2017).
European Search Report dated May 21, 2021 of European counterpart application No. EP 20207380.5.

* cited by examiner

TECHNIQUE FOR CONTROLLING A HUMAN MACHINE INTERFACE

CROSS REFERENCE TO RELATED APPLICATIONS

This application claims priority to European patent application 20 207 380.5, filed Nov. 13, 2020, the entire content of which is incorporated herein by reference.

TECHNICAL FIELD

The present disclosure relates to a technique for controlling a human machine interface (HMI). More specifically, and without limitation, methods and devices are provided for controlling an HMI for two interconnected tasks comprising performance measurement means for cognitive training of assessing physical objects.

BACKGROUND

Controlling an HMI for cognitive training may comprise different tasks (also: "trainings").

The document US 2017/0098385 A1 describes a system for personalized cognitive training with difficulty progression, in which a cognitive assessment of a human user with (e.g., age-related) cognitive decline is performed for determining a maximal performance of the user related to a set of assessment tasks, based on which a performance range is determined and a first progress gate comprising a first assessment task is selected. As a task difficulty progresses, further progress gates comprising further assessment tasks are selected.

The document U.S. Pat. No. 9,881,515 B2 describes a system for sensory and cognitive skill development (e.g., for selective attention and auditory discrimination or reading and language production) based on varying music-based tasks for a human user, which as an example task comprises matching sound probes to visual probes after audiovisual cue stimuli had been shown.

However, a cognitive training aimed at (consciously and/or subconsciously) modifying a perceived value and/or valuation of and/or a reward response to items (e.g., physical objects) is neither foreseen in the document US 2017/0098385 A1 nor in the document U.S. Pat. No. 9,881,515 B2.

In a task called "Go/NoGo", a human user is instructed to respond as fast as possible to a given category of items and to withhold his/her responses to another category. Such practice can act as motivational conditioning paradigm which can eventually automatize the engagement of inhibition processes via associative cognitive learning mechanisms. By performing the Go/NoGo task, the perceived value of, a behavioral response to and/or a brain response to the items may be reduced. When a NoGo item (also denoted as "stimulus") becomes associated with avoidance and/or aversion, its presentation can (e.g., directly) trigger the avoidance and/or aversive center, which can suppress the activation of the approach center (e.g., appetitive center for food items) of the user. This mechanism can decrease a hedonic and motivational value of the NoGo stimuli and thus the behavioral response and/or brain response to the stimuli, as reviewed for example by H. Veling et al. in Curr. Addict. Rep., vol. 4, no. 1, pp. 35-41 (2017).

In Cued Approach Training (CAT), items are displayed for a short period during which a Go-cue prompting a motor response can be presented. The task of a human user is to (e.g., only) respond to cued items before they are offset or disappear. Since task performance is improved by paying attention to and rapidly reaching the items associated with the cues (but not to those not associated with the cue), attention and approach tendency can automatically be allocated to the cued items. In turn, the target items saliency and perceived value increases as well as their consumption, as reviewed for example by Kakoschke et al. in Addict. Behav., vol. 64, pp. 21-28, (January 2017).

Performing conventional cognitive training by either a Go/NoGo task or a CAT is subject to two main limitations.

Firstly, the training or task parameters in previous interventions can limit their efficacy. Conventionally, any one of a Go/NoGo task and a CAT involves a short training session and/or uses a training task with limited individual adjustments of the target items to a human user's predilections, tastes or difficulty levels. In addition, the task environment is typically not engaging, preventing adherence and engagement in the cognitive training. If anything, the cognitive training effect is conventionally minimized by presenting the task in weakly motivating task environments.

Secondly, conventional (e.g., food-related) behavioral decision training does not fully control for a human user's expectations. Causal inferences on the effectiveness of training tasks can only be drawn when they are contrasted with control conditions differing only at the level of their active input (i.e. mechanism of action), which in the case of (e.g., food-related) behavioral decision training is the motor control of responses to the target (e.g., food) items. Yet, conventional control tasks use unrelated (e.g., non-food) images and/or tasks that relate weakly to executive motor control, such as tasks without inhibition toward the targeted items. Users in a different (e.g., denoted as "control" and "experimental") group can have different expectations regarding the effect of a cognitive training of the task on (e.g., food-related) behaviors or on executive control performance. Hence, expectations can confound any differences between the groups in (e.g., food) item valuation or consumption outcomes and the effectiveness of the cognitive training.

SUMMARY

Accordingly, there is a need for a technique for controlling a human machine interface (HMI) that provides cognitive training for (e.g., subconsciously) alternating and/or reinforcing a declination of one or more categories of physical objects (e.g., unhealthy food items) while (e.g., subconsciously) alternating and/or reinforcing a predilection of one or more further categories of physical objects (e.g., healthy food items). A Declination of a category of physical objects may also be denoted as a devaluation of and/or behavior away from the category of physical objects. Alternatively or in addition, a predilection of a category of physical objects may also be denoted as perceived value of or behavior towards the category pf physical objects.

Alternatively or in addition, there is a need for a technique for controlling a HMI that provides (e.g., unconscious) bias training towards one or more categories of physical objects (e.g., healthy food items) and away from one or more further categories of physical objects (e.g., unhealthy food items). Further alternatively or in addition, the HMI controlling technique disclosed herein enables associating motoric inhibition with one or more categories of physical objects (e.g., unhealthy food items) while increasing bias attention and/or approach tendency to one or more further categories of physical objects (e.g., healthy food items).

As to a first method aspect, a method of controlling an HMI is provided. The method comprises or initiates a step of outputting, using the HMI, a predefined criterion applicable to each of a plurality of physical objects in a first task. Each of the plurality of physical objects is associated with a category within a group of at least two pairwise disjoint categories. The predefined criterion is fulfilled for each physical object associated with a first category within the group of categories. The predefined criterion is not fulfilled for each physical object associated with a second category within the group of categories. The controlling of the HMI for the first task comprises repeatedly performing (e.g., in consecutive order) the steps of rendering, using the HMI, a physical object out of the plurality of physical objects; monitoring the HMI for an input during a predefined first time period after the rendering of the physical object; and updating a first metric comprising a first sub-metric and a second sub-metric indicative of a performance measurement in the first task.

The first sub-metric of the first metric is increased if the input is received within the first time period and if the displayed physical object fulfills the predefined criterion. Alternatively or in addition, the first sub-metric of the first metric is increased if the input is absent within the first time period and if the displayed physical object does not fulfill the predefined criterion. Further alternatively or in addition, the second sub-metric of the first metric is decreased if the input is received within the first time period and if the displayed physical object does not fulfill the predefined criterion. Still further alternatively or in addition, the second sub-metric of the first metric is decreased if the input is absent within the first time period and if the displayed physical object fulfills the predefined criterion.

The method further comprises or initiates a step of rendering, using the HMI, a plurality of receptacles each enclosing one of the plurality of physical objects for a second task. The controlling of the HMI for the second task comprises repeatedly performing the steps of rendering a physical object out of the plurality of physical objects at any one of the receptacles for a predefined second time period; selectively rendering, using the HMI, a cue at the rendered physical object within the second time period; monitoring the HMI for an input responsive to the rendering of the physical object and/or responsive to the rendering of the cue within the second time period; and updating a second metric comprising a first sub-metric and a second sub-metric indicative of a performance measurement in the second task.

The first sub-metric of the second metric is increased if the input is received within the second time period at the position of the selectively rendered cue. Alternatively or in addition, the first sub-metric of the second metric is increased if the input is absent within the second time period and if no cue was selectively rendered. Further alternatively or in addition, the second sub-metric of the second metric is decreased if the input at the position of the physical object is received within the second time period and if no cue was selectively rendered. Still further alternatively or in addition, the second sub-metric of the second metric is decreased if the input is absent within the second time period and the cue was selectively rendered.

The HMI may comprise a touchscreen and optionally one or more speakers. Alternatively or in addition, the HMI may comprise a virtual reality (VR) headset and motion sensors (e.g., of the VR headset).

The predefined criterion may be a binary property that each of the plurality of physical objects may either have or not have. For example, the plurality of physical objects may comprise food items. Alternatively or in addition, the binary property may comprise either one of "sweet" or "salty". Further alternatively or in addition, the predefined criterion may comprise providing at least one of a "go" and a "no go" cue, e.g. a green circle and/or a red circle, respectively, surrounding (e.g. encircling) the physical object.

A category may also be denoted as a sub-group.

Two pairwise disjoint categories within a group comprising at least three different pairwise disjoint categories may fulfill the same predefined criterion. For example, food items may be assembled in four categories comprising "sweet and healthy", "sweet and unhealthy", "salty and healthy" and "salty and unhealthy". Alternatively or in addition, a first category fulfilling the predefined criterion (e.g., "sweet") may comprise two combined properties (e.g., "sweet and healthy"), and a second category not fulfilling the predefined criterion may comprise two combined properties, both of which differ from the two combined properties of the first category (e.g., the second category may comprise "salty and unhealthy").

Controlling the HMI for the first task repeatedly may comprise repeating the steps (e.g., consecutively) of rendering a physical object, monitoring for an input after rendering the physical object and updating the first metric.

In each repetition of the first task and/or of the second task, the choice of a physical object rendered from within the plurality of physical objects may be independent of the choice of a physical object of any one of the previous repetitions. Alternatively or in addition, the choice of a physical object to be rendered may be based on a pseudo-random number generator (e.g. within one category fulfilling the criterion and another category not fulfilling the criterion and a predefined ratio among the categories).

The predefined first time period of the first task and/or the predefined second time period of the second task may comprise two different predefined time sub-periods. For example, within a predefined first time sub-period, a physical object may be rendered. After the expiry of the predefined first time sub-period, the HMI may still be monitored for the input until a predefined second time sub-period has expired. The expiry of the predefined second time sub-period may be later than the expiry of the predefined first time sub-period. The update of each of the first and the second sub-metric of the respective metric may only be performed after the expiry of the predefined second time sub-period.

An input received if the displayed physical object fulfills the predefined criterion may also be denoted as "correct input" (e.g., within the respective predefined first time sub-period of the respective task). An absent input if the displayed physical object does not fulfill the predefined criterion may also denoted as "correct non-input" (e.g., within the respective predefined first time sub-period). Alternatively or in addition, an input to a task received after the expiry of the respective predefined first time sub-period, but before the expiry of the respective predefined second time sub-period may be denoted as "correct late input".

The first sub-metric of the first metric and/or of the second metric may be increased by a predefined amount depending on the time of the correct input for the respective task. For example, if the correct input is received within the first time sub-period of the predefined respective time period, the amount for increasing the first sub-metric may be larger than if the correct input is received after the expiry of the first time sub-period but before the expiry of the second time sub-period. Alternatively or in addition, the predefined amount of increasing the first sub-metric may increase with the number of correct inputs (e.g., not comprising correct late inputs) and/or with the time of (e.g., continuously) performing the respective task.

Alternatively of in addition, the first sub-metric of the respective metric (e.g., the respective metric being the first metric and/or the second metric) may comprise two sub-sub-metrics. A first sub-sub-metric of the first sub-metric may comprise a level and/or difficulty (also: difficulty level) of performing the respective task. The level may increase at reaching and/or after exceeding a predefined number (e.g., five or six) of correct inputs.

Alternatively or in addition, a second sub-sub-metric of the first sub-metric of the respective metric may comprise a score indicative of (e.g., number of) correct inputs, optionally depending on the level. For example, the score may increase by a first number (e.g., ten) for each correct input at a first level and by a second number higher than the first number (e.g., eleven) for each correct input at a second level (which is, e.g., in terms of difficulty consecutive to and higher than the first level).

The score of one task (e.g., the first task) may be decreased by a predefined amount for increasing (e.g., a sub-sub-metric or a "gauge" of) the second sub-metric of the other task (e.g., the second task).

Alternatively or in addition, the second sub-metric of the first metric and/or of the second metric may comprise at least two sub-sub-metrics (also denoted as and/or represented by "gauges"). For example, a first gauge of the second sub-metric may be indicative of an accuracy (also: "correctness") of the input for the respective task, and a second gauge of the second sub-metric may be indicative of a speed of the input (e.g., distinguishing a "correct late input" from a "correct input") for the respective task.

Rendering a physical object from at least one category may comprise displaying of a (e.g., healthy) food item.

Each of the plurality of receptacles rendered for the second task may alternatively be denoted as container, box or housing. For example, any one of the receptacles may be embodied by a cardboard box (e.g., as used for baked food items).

A receptacle enclosing a physical object may comprise the physical object being invisible and/or imperceptible at the HMI.

Rendering a physical object at any one of the receptacles may comprise opening the receptacle and/or rendering the receptacle transparent. Alternatively or in addition, rendering a physical object at any one of the receptacles may comprise stopping to render the receptacle and rendering the physical object instead, e.g. at the same place of a touch-screen or of a display of a VR headset. Further alternatively or in addition, rendering a physical object at any one of the receptacles may comprise overlaying two images, e.g., with the physical object rendered in the foreground and the receptacle at least partially rendered in the background.

By the controlling of the HMI for the first task and for the second task comprising repeatedly (e.g., consecutively) performing the steps of each of the respective tasks, a cognitive training may be achieved.

By the first task (also denoted as "Go/No training" or briefly "GNG"), a reduction of a value and/or a valuation of physical objects (e.g., unhealthy food items) comprised in one or more categories can be accomplished by associating them with motoric inhibition. Alternatively or in addition, by the second task (also denoted as "Cue Approach Training" or briefly "CAT") an increase in a value and/or a valuation of physical objects (e.g., healthy food items) comprised in one or more further categories can be accomplished by biasing attention and approach tendency toward them.

The effectiveness of the technique can be maximized by enhancing motivation and adherence of a human user of the HMI. Motivation and adherence can be enhanced by the use of (e.g., various sub-sub-metrics of) the first and second metrics of the respective tasks. For example, the first sub-metric of the respective metric may comprise a score as a sub-sub-metric, which may be associated with a reward mechanism. Alternatively or in addition, by the predefined (e.g., depending on a difficulty level) time periods and/or by one or more gauges as sub-sub-metrics of the respective second sub-metric an intrinsic challenge can be introduced. Further alternatively or in addition, a social challenge can be implemented by a feedback on the updates of the first metric and the second metric reported to an external controller. The external controller may provide the feedback to a user by comparing the reported updates of the first metric and the second metric with tabulated and/or stored values (e.g., comprising reported values from a plurality of other users). Still further alternatively or in addition, motivation and adherence can be enhanced by an advantageous visual and/or auditory (e.g., audiovisual) task environment.

Progressive difficulty levels can ensure that the first task and the second task remain adapted to a human user's performance (e.g., an improvement thereof). Alternatively or in addition, the first task and the second task can be individualized and/or personalized to each user's predilections and/or dislikes (e.g., tastes and/or eating habits) by specifically targeting his/her preferred categories of physical objects (e.g., high-density energy food items), as measured with palatability scales at the beginning of controlling the HMI by the user for the first time.

The first task may be repeated consecutively for a predefined third time period. Alternatively or in addition, the second task may be repeated consecutively for a predefined fourth time period. Optionally, the third time period and the fourth time period may have equal length.

The first task may be repeated (e.g., consecutively) for a predefined third time period (e.g., ten minutes) on a daily and/or workday basis (e.g., the first task may be repeated consecutively for ten minutes on five days per week). Alternatively or in addition, the second task may be repeated (e.g., consecutively) for a predefined fourth time period (e.g., ten minutes) on a daily and/or workday basis (e.g., the second task may be repeated consecutively for ten minutes on five days per week).

Repeating (e.g., consecutively) the first task and/or the second task may alternatively be denoted as performing a run and/or a session of the first task and/or the second task, respectively. Alternatively or in addition, a run and/or a session may correspond to repeating (e.g., consecutively) the first task and/or the second task in one day.

The temporal ordering of repeatedly performing the first task and repeatedly performing the second task may be arbitrary (e.g., it may be randomly switched from one day to another).

The first task and the second task may be repeatedly performed for a predefined number of runs and/or sessions. Alternatively or in addition, the first task and the second task may be repeatedly performed for a predefined number of days and/or weeks (e.g., 20 workdays and/or four weeks).

The predefined first time period and/or a time of rendering the cue within the predefined second time period may decrease with a value of the first sub-metric of the respective metric indicative of the performance measurement of the respective task. Alternatively or in addition, the predefined first time period and/or a time of rendering the cue within the predefined second time period may decrease with a number of repetitions of the respective task. Further alternatively or in addition, the predefined first time period and/or a time of rendering the cue within the predefined second time period may decrease with a number of performances of the method comprising repetitions of the first task and of the second task.

The number of performances of the method may also be denoted as the number of runs and/or sessions and/or days on which both the first task and the second task are performed (e.g., for a predefined respective time period, in particular for ten minutes per day per task). Alternatively or in addition, the number of (e.g., consecutive) repetitions of the respective task may comprise the number of repetitions of the task within a run and/or session and/or day.

Decreasing the respective time period for monitoring the HMI for an input in the respective task may also be denoted as increasing the difficulty and/or increasing the level of the respective task.

The respective time period for monitoring the HMI for an input in the respective task may decrease with the number of correct inputs (e.g., not comprising correct late inputs) within the respective tasks (e.g., within a run, session or day). Alternatively or in addition, the first sub-metric of the respective metric for a task may comprise a count and/or value of the number of correct inputs within a run, session or day. The difficulty of the respective task may increase (e.g., the time period for an input may decrease) if a predefined count and/or predefined value of the number of correct inputs (e.g., after every five or six correct inputs) is reached and/or exceeded within a run, session or day.

Each of the second sub-metric of the first metric and the second sub-metric of the second metric may correspond to or may be represented by at least one gauge. Each gauge may comprise a predetermined maximum and a predetermined minimum. At each start of repeatedly controlling the HMI for the respective task, each of the at least one gauge of the respective task may be filled or set to the predetermined maximum. The repeatedly controlling of the HMI for the respective task may terminate if at least one of the at least one gauge of the respective task is emptied to or reaches the predetermined minimum.

The start of repeatedly controlling the HMI for the task may correspond to the start of a session and/or a run. Terminating the repeatedly controlling of the HMI for the respective task may also be denoted as stopping the session and/or the run.

Controlling the HMI for the first task may further comprise a step of modifying the predetermined maximum and/or an initial state or filling of the at least one gauge corresponding to or representing the second sub-metric of the first metric before repeatedly controlling the HMI for the first task based on a value of the first sub-metric of the second metric. Alternatively or in addition, controlling the HMI for the second task may further comprise a step of modifying the predetermined maximum and/or an initial state or filling of the at least one gauge corresponding to or representing the second sub-metric of the second metric before repeatedly controlling of the HMI for the second task based on a value of the first sub-metric of the first metric.

For example, an initial state of a gauge (e.g., one of two gauges and/or of multiple sub-sub-metrics associated to the second sub-metric of the first metric) indicative of the accuracy and/or correctness of an input of the first task may be increased based on the value of the first sub-metric (e.g., a score as a sub-sub-metric) of the second metric of the second task (e.g., while decreasing the value of the first sub-metric, in particular a value of a sub-sub-metric such as a score, of the second metric by a predefined amount).

The increase of the at least one first gauge may be performed at the beginning of a run and/or session and/or before (e.g., consecutively) repeating the HMI controlling steps of the first task. Alternatively or in addition, the at least one first gauge may increase periodically (e.g., every ten seconds or every twenty seconds) while (e.g., consecutively) repeating the HMI controlling steps of the first task.

Alternatively or in addition, an initial state of a gauge (e.g., one of two gauges and/or of multiple sub-sub-metrics associated to the second sub-metric of the second metric) indicative of the accuracy and/or correctness of the input of the second task may be increased based on a value of the first sub-metric (e.g., a score as a sub-sub-metric) of the first metric of the first task (e.g., while decreasing the value of the first sub-metric, in particular a value of a sub-sub-metric such as a score, of the first metric by a predefined amount).

The increase of the at least one second gauge may be performed at the beginning of a run and/or session and/or before (e.g., consecutively) repeating the HMI controlling steps of the second task. Alternatively or in addition, the at least one second gauge may increase periodically (e.g., every ten seconds or every twenty seconds) while (e.g., consecutively) repeating the HMI controlling steps of the second task.

The at least one gauge corresponding to or representing the second sub-metric of the first metric may comprise a gauge indicative of an accuracy of the input for the first task. Alternatively or in addition, the at least one gauge corresponding to or representing the second sub-metric of the first metric may comprise a gauge indicative of the speed of the input for the first task. Further alternatively or in addition, the at least one gauge corresponding to or representing the second sub-metric of the second metric may comprise a gauge indicative of an accuracy of the input for the second task. Still further alternatively or in addition, the at least one gauge corresponding to or representing the second sub-metric of the second metric may comprise a gauge indicative of the speed of the input for the second task.

The gauge indicative of accuracy in the first metric may be decreased if the input is received within the first time period and if the displayed physical object does not fulfill the predefined criterion. Alternatively or in addition, the gauge indicative of speed in the first metric may be decreased if the input is absent within the first time sub-period of the first time period, but is received within the second time sub-period of the first time period, and if the displayed physical object fulfills the predefined criterion.

The gauge indicative of accuracy in the second metric may be decreased if the input at the position of the physical object is received within the second time period and if no cue was selectively rendered. Alternatively or in addition, the gauge indicative of speed in the second metric may be decreased if the input is absent within the first time sub-period of the second time period, but is received within the second time sub-period of the second time period, and the cue was selectively rendered.

The method may further comprise a step of configuring the HMI by assembling the categories of the plurality of physical objects based on an initial configuration input for each of an extended plurality of physical objects comprising the plurality of physical objects.

The initial configuration input may comprise collecting preferences (also denoted as predilections or tastes) of a user. For example, the user may be asked to assess a taste of a plurality of food items (e.g., an inclination ranging from "like very much" to "do not like at all") on a Likert scale.

Responsive to the initial configuration input, a (e.g., sub-) group and/or (e.g., sub-) plurality from an extended group and/or an extended plurality of physical objects may be configured for use in the first task and in the second task. The initial configuration input may also be referred to as initial assessment input.

The step of configuring the HMI may be performed initially, e.g., once before the first run and/or the first session and/or on the first day of performing the method.

Alternatively or in addition, a final configuration input may be received after the last run and/or the last session and/or at the end of the last day of performing the method. The final configuration input may also be referred to as final assessment input. Optionally, the initial assessment input and the final assessment input may be compared.

The method may further comprise a step of receiving a final configuration input for each of the plurality of physical objects. The method may still further comprise a step of outputting a comparison of the initial configuration input and the final configuration input.

Outputting the comparison of the initial assessment input and the final assessment input may also be denoted as evaluating the effectiveness of performing the method.

The input may comprise a gesture moving (e.g., fixating and/or dragging) the physical object for the first task. Alternatively or in addition, the input may comprise a physical contact (e.g., a touch) with the rendered physical object for the second task. Further alternatively or in addition, the input may comprise a selection of a mark on a scale for the configuring of the HMI.

The gesture moving the physical object may alternatively be denoted as dragging the physical object. For example, a correct input may comprise moving the physical object from its position of rendering to a predefined further position and/or to a predefined range of further positions. An incorrect input may comprise terminating the gesture before the physical object has reached the predefined further position and/or the predefined range of further positions. Alternatively or in addition, prematurely terminating the gesture may also be denoted as dropping the physical object.

The cue of the second task may comprise an audiovisual signal.

The cue may, e.g., comprise a (typically colored, in particular green) circle around the rendered physical object. Alternatively or in addition, the cue may comprise an acoustic alert (e.g., simultaneously outputted with a visual cue such as a circle).

The HMI may be in data communication with an external controller for reporting a tag indicative of the HMI and/or indicative of a user of the HMI. Alternatively or in addition, the HMI may be in data communication with an external controller for reporting configuring the HMI (e.g., as described above). Further alternatively or in addition, the HMI may be in data communication with an external controller for reporting a time indicative of controlling the HMI repeatedly for the first task and/or for the second task. Still further alternatively or in addition, the HMI may be in data communication with an external controller for reporting the updates of the first metric and of the second metric. Optionally, the external controller may trigger a notification if the updates of the first metric and of the second metric deviate from a predefined schedule.

The external controller may be external to the device. The data communication may comprise a network link, e.g., via the Internet.

The external controller may be configured to receive reports on updates of the first metric and of the second metric (e.g., comprising updates of the scores, levels and/or performing times reached within the first task and/or the second task) from a plurality of HMIs and/or a plurality of users. Each HMI and/or each user of the HMI may be identified and/or identifiable by a tag (also: "code").

Alternatively or in addition, the external controller may compare the updates of the first metric and of the second metric of an HMI and/or a user (e.g., comprising updates of the scores, levels and/or performing times reached within the first task and/or the second task) with a list and/or with a table. The list and/or the table may be stored locally at the external controller. Alternatively or in addition, the list and/or the table may comprise predefined values of the first metric and of the second metric and/or a collection of reported values of the first metric and the second metric from a plurality of HMIs and/or users (e.g., comprising updates of the scores, levels and/or performing times reached within the first task and/or the second task).

The time indicative of controlling the HMI repeatedly for the first task and/or for the second task may comprise a total time of repeatedly performing each task (e.g., per session, run and/or day and/or summed over all sessions, runs and/or days). The total time of repeatedly performing each task may also denoted as "overall time" or "performing time" of each task.

The updates of the first metric and of the second metric may comprise a (e.g., average) response time per task.

The external controller may be configured to provide a feedback to a user of the HMI responsive to the reported updates of the first metric and/or of the second metric.

The feedback to the user of the HMI may be transmitted over an alternative data connection. For example, the feedback may be provided by e-mail or short message service (SMS) to the user. Alternatively or in addition, the feedback may be indicative of a performance relative to a control group and/or a group of other users. Further alternatively or in addition, the feedback may be indicative of the steps of the first task being (e.g. consecutively) repeated for less than the predefined third time period (e.g., less than ten minutes per day) and/or the steps of the second task being (e.g., consecutively) repeated for less than the predefined fourth time period (e.g., less than ten minutes per day).

Repeating a task (e.g., consecutively) for less than the respective predefined time period may alternatively be denoted as failing the task.

As to another aspect, a computer program product is provided. The computer program product comprises program code portions for performing any one of the steps of the method aspect disclosed herein when the computer program product is executed on one or more computing devices. The computer program product may be optionally stored on a computer-readable recording medium. The computer program product may also be provided for download, e.g., via a radio network, a radio access network (RAN), the Internet and/or a host computer. Alternatively, or in addition, the method may be encoded in a Field-Programmable Gate Array (FPGA) and/or an Application-Specific Integrated Circuit (ASIC), or the functionality may be provided for download with a hardware description language.

As to a device aspect, a device for controlling a human machine interface (HMI) is provided. The device comprises the HMI and processing circuitry configured to perform any one of the steps of the method aspect disclosed herein. Alternatively, or in addition, the device may comprise a predefined criterion outputting unit that is configured to output, using the HMI, a predefined criterion applicable to each of a plurality of physical objects in a first task, wherein each of the plurality of physical objects is associated with a category within a group of at least two pairwise disjoint categories and the predefined criterion is fulfilled for each physical object associated with a first category within the group of categories and the predefined criterion is not fulfilled for each physical object associated with a second category within the group of categories.

The device may further comprise a first task controlling unit configured to repeatedly perform the (e.g., consecutive) steps of rendering, using the HMI, a physical object out of the plurality of physical objects; monitoring the HMI for an input during a predefined first time period after the rendering of the physical object; and updating a first metric comprising a first sub-metric and a second sub-metric indicative of a performance measurement in the first task. The first sub-metric of the first metric is increased if the input is either received within the first time period and if the displayed physical object fulfills the predefined criterion, or if the input is absent within the first time period and if the displayed physical object does not fulfill the predefined criterion. The second sub-metric of the first metric is decreased if the input is either received within the first time period and if the displayed physical object does not fulfill the predefined criterion, or if the input is absent within the first time period and if the displayed physical object fulfills the predefined criterion.

The device may further comprise a receptacles rendering unit that is configured to render, using the HMI, a plurality of receptacles each enclosing one of the plurality of physical objects for a second task.

The device may still further comprise a second task controlling unit that is configured to repeatedly perform the (e.g., consecutive) steps of rendering a physical object out of the plurality of physical objects at any one of the receptacles for a predefined second time period; selectively rendering, using the HMI, a cue at the rendered physical object within the second time period; monitoring the HMI for an input responsive to the rendering of the physical object within the second time period; and updating a second metric comprising a first sub-metric and a second sub-metric indicative of a performance measurement in the second task. The first sub-metric of the second metric is increased if the input is either received within the second time period at the position of the selectively rendered cue, or if the input is absent within the second time period and if no cue was selectively rendered. The second sub-metric of the second metric is decreased if the input at the position of the physical object is either received within the second time period and if no cue was selectively rendered, or if the input is absent within the second time period and the cue was selectively rendered.

As to a further device aspect, a device for controlling a human machine interface (HMI) is provided. The device comprises processing circuitry (e.g., at least one processor) and a memory. Said memory may comprise (e.g., may be operable to store) instructions executable by said processing circuitry whereby the device is operative to control the HMI for the first task and to control the HMI for the second task.

Controlling the HMI for the first task may comprise outputting, using the HMI, a predefined criterion applicable to each of a plurality of physical objects, wherein each of the plurality of physical objects is associated with a category within a group of at least two pairwise disjoint categories and the predefined criterion is fulfilled for each physical object associated with a first category within the group of categories and the predefined criterion is not fulfilled for each physical object associated with a second category within the group of categories. Controlling the HMI for the first task may further comprise repeatedly performing the steps of rendering, using the HMI, a physical object out of the plurality of physical objects; monitoring the HMI for an input during a predefined first time period after the rendering of the physical object; and updating a first metric comprising a first sub-metric and a second sub-metric indicative of a performance measurement in the first task. The first sub-metric of the first metric may be increased if the input is received within the first time period and if the displayed physical object fulfills the predefined criterion. Alternatively or in addition, the first sub-metric of the first metric may be increased if the input is absent within the first time period and if the displayed physical object does not fulfill the predefined criterion. Further alternatively or in addition, the second sub-metric of the first metric may be decreased if the input is received within the first time period and if the displayed physical object does not fulfill the predefined criterion. Still further alternatively or in addition, the second sub-metric of the first metric may be decreased if the input is absent within the first time period and if the displayed physical object fulfills the predefined criterion.

Controlling the HMI for the second task may comprise rendering, using the HMI, a plurality of receptacles each enclosing one of the plurality of physical objects. Controlling the HMI for the second task may further comprise repeatedly performing the steps of rendering a physical object out of the plurality of physical objects at any one of the receptacles for a predefined second time period; selectively rendering, using the HMI, a cue at the rendered physical object within the second time period; monitoring the HMI for an input responsive to the rendering of the physical object within the second time period; and updating a second metric comprising a first sub-metric and a second sub-metric indicative of a performance measurement in the second task. The first sub-metric of the second metric may be increased if the input is received within the second time period at the position of the selectively rendered cue. Alternatively or in addition, the first sub-metric of the second metric may be increased if the input is absent within the second time period and if no cue was selectively rendered. Further alternatively or in addition, the second sub-metric of the second metric may be decreased if the input at the position of the physical object is received within the second time period and if no cue was selectively rendered. Still further alternatively or in addition, the second sub-metric of the second metric may be decreased if the input is absent within the second time period and the cue was selectively rendered.

The device may be further operative to perform any one of the steps of the method aspect disclosed herein.

As to a still further aspect, a system for controlling a human machine interface (HMI) is provided. The system comprises a plurality of devices according to the device aspect disclosed herein. Alternatively or in addition, the system comprises an external controller configured for data communication with each of the devices as disclosed herein. The data communication may be configured for receiving the updates of the first metric and the second metric from each of the devices at the external controller, and optionally for triggering a notification to any one of the devices. Further alternatively or in addition, the system comprises a storage server configured to store the updates of the first metric and the second metric for each of the devices as disclosed herein and for providing feedback to a user of each of the devices.

Any of the devices may be a mobile or wireless device, e.g., a 3GPP user equipment (UE) or a Wi-Fi station (STA). The device may be a mobile or portable station. Examples for the UE and the mobile station include a mobile phone (e.g., a smartphone) and a tablet computer. Examples for the portable station include a laptop computer and a television set. Alternatively or in addition, the device may comprise a VR headset and motion sensors (e.g., of the VR headset).

Any of the devices disclosed herein may be wirelessly connected or connectable (e.g., according to the 3GPP Standard, Wi-Fi, Bluetooth, ZigBee or Z-Wave) with the external controller. Herein, the external controller may encompass any station that is configured to provide radio access to any of the devices. Alternatively or in addition, the external controller may provide a data link to the storage server for storing updates and/or for providing feedback.

The channel or link used for the data transmission and the radio reception, i.e., the channel between any of the devices disclosed herein and the external controller may comprise multiple subchannels or subcarriers (as a frequency domain). Alternatively or in addition, the channel or link may comprise one or more slots for a plurality of modulation symbols (as a time domain). Alternatively or in addition, the channel or link may comprise a directional transmission (also: beamforming transmission) at the transmitter, a directional reception (also: beamforming reception) at the receiver or a multiple-input multiple-output (MIMO) channel with two or more spatial streams (as a spatial domain).

Any of the devices disclosed herein and the external controller may be spaced apart. Any of the devices disclosed herein and the external controller may be in data or signal communication exclusively with the radio communication.

In any aspect, any of the devices and the external controller may form, or may be part of, a radio network, e.g., according to the Third Generation Partnership Project (3GPP) or according to the standard family IEEE 802.11 (Wi-Fi). The radio network may be a radio access network (RAN) comprising one or more base stations. Alternatively, or in addition, the radio network may be a vehicular, ad hoc and/or mesh network. The method aspect may be performed by one or more embodiments of the device in the radio network.

The RAN may be implemented according to the Global System for Mobile Communications (GSM), the Universal Mobile Telecommunications System (UMTS), 3GPP Long Term Evolution (LTE) and/or 3GPP New Radio (NR).

The system may further comprise a host computer. The processing circuitry of the host computer may be configured to execute a host application, thereby providing the user data and/or any host computer functionality described herein, e.g., comprising the storage server. Alternatively, or in addition, the processing circuitry of the UE may be configured to execute a client application associated with the host application.

Any one of the devices, the external controller, the storage server, or the system for embodying the technique may further include any feature disclosed in the context of the method aspect, and vice versa. Particularly, any one of the units and modules, or a dedicated unit or module, may be configured to perform or initiate one or more of the steps of the method aspect.

BRIEF DESCRIPTION OF THE DRAWINGS

The disclosure will now be described with reference to the drawings wherein.

DESCRIPTION OF EXEMPLARY EMBODIMENTS

In the following description, for purposes of explanation and not limitation, specific details are set forth, such as a specific human machine interface (HMI) and a specific network environment in order to provide a thorough understanding of the technique disclosed herein. It will be apparent to one skilled in the art that the technique may be practiced in other embodiments that depart from these specific details. Moreover, while the following embodiments are primarily described for a tablet computer or smartphone as a device and a New Radio (NR) or 5G implementation for a data connection, it is readily apparent that the technique described herein may also be implemented for any other radio communication technique, including 3GPP LTE (e.g., LTE-Advanced or a related radio access technique such as MulteFire), in a Wireless Local Area Network (WLAN) according to the standard family IEEE 802.11, for Bluetooth according to the Bluetooth Special Interest Group (SIG), particularly Bluetooth Low Energy, Bluetooth Mesh Networking and Bluetooth broadcasting, for Z-Wave according to the Z-Wave Alliance or for ZigBee based on IEEE 802.15.4. Alternatively or in addition, the data connection may implementable by a wired communication technique.

Moreover, those skilled in the art will appreciate that the functions, steps, units and modules explained herein may be implemented using software functioning in conjunction with a programmed microprocessor, an Application Specific Integrated Circuit (ASIC), a Field Programmable Gate Array (FPGA), a Digital Signal Processor (DSP) or a general purpose computer, e.g., including an Advanced RISC Machine (ARM). It will also be appreciated that, while the following embodiments are primarily described in context with methods and devices, the disclosure may also be embodied in a computer program product as well as in a system comprising at least one computer processor and memory coupled to the at least one processor, wherein the memory is encoded with one or more programs that may perform the functions and steps or implement the units and modules disclosed herein.

Figure 1:
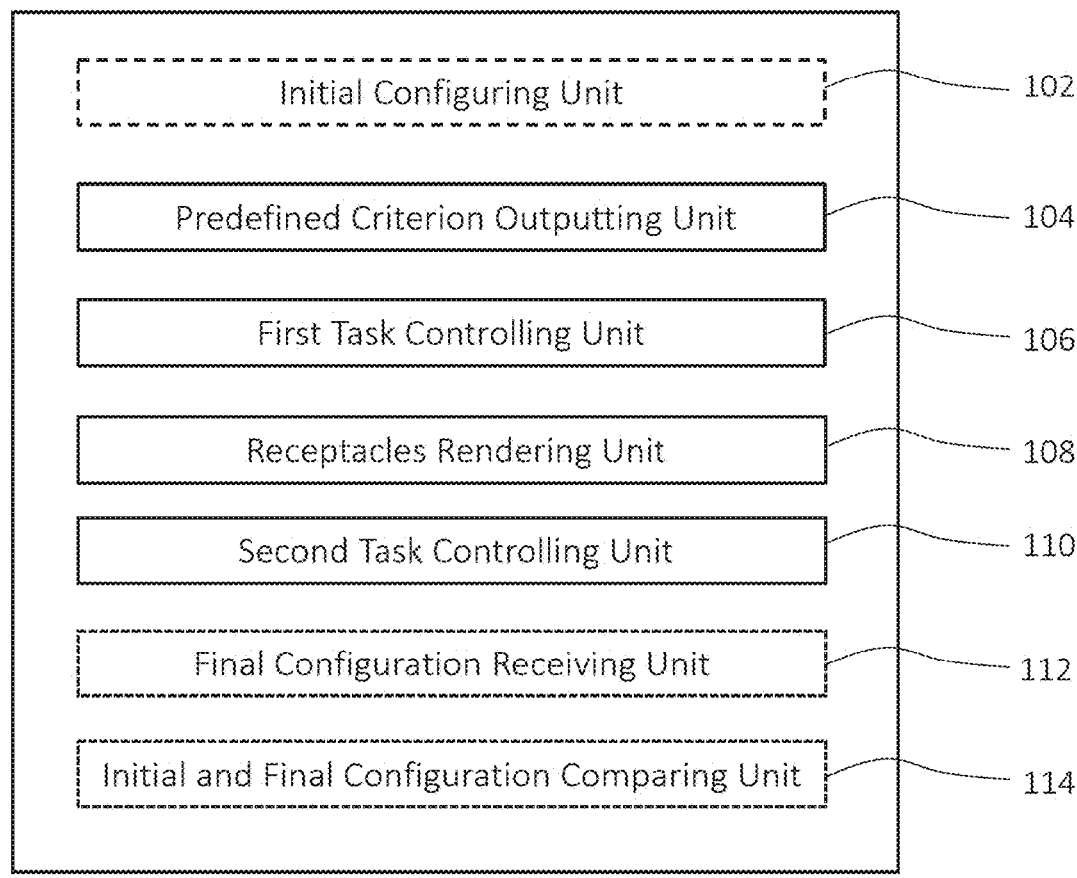
FIG. 1 shows a schematic block diagram of an embodiment of a device for controlling a human machine interface (HMI)

FIG. 1 schematically illustrates an example block diagram of a device for controlling a human machine interface (HMI). The device is generically referred to by reference sign 100.

The device 100 comprises a predefined criterion outputting unit 104 that is configured to output, using the HMI, a predefined criterion applicable to each of a plurality of physical objects in a first task, wherein each of the plurality of physical objects is associated with a category within a group of at least two pairwise disjoint categories and the predefined criterion is fulfilled for each physical object associated with a first category within the group of categories, and the predefined criterion is not fulfilled for each physical object associated with a second category within the group of categories.

The device 100 further comprises a first task controlling unit 106 configured to repeatedly perform the (e.g., consecutive) steps of rendering, using the HMI, a physical object out of the plurality of physical objects; monitoring the HMI for an input during a predefined first time period after the rendering of the physical object; and updating a first metric comprising a first sub-metric and a second sub-metric indicative of a performance measurement in the first task.

The first sub-metric of the first metric is increased, if the input is received within the first time period and if the displayed physical object fulfills the predefined criterion, and/or if the input is absent within the first time period and if the displayed physical object does not fulfill the predefined criterion.

The second sub-metric of the first metric is decreased, if the input is received within the first time period and if the displayed physical object does not fulfill the predefined criterion, and/or if the input is absent within the first time period and if the displayed physical object fulfills the predefined criterion.

The device 100 further comprises a receptacles rendering unit 108 that is configured to render, using the HMI, a plurality of receptacles each enclosing one of the plurality of physical objects for a second task.

The device 100 still further comprises a second task controlling unit 110 that is configured to repeatedly perform the (e.g., consecutive) steps of rendering a physical object out of the plurality of physical objects at any one of the receptacles for a predefined second time period; selectively rendering, using the HMI, a cue at the rendered physical object within the second time period; monitoring the HMI for an input responsive to the rendering of the physical object within the second time period; and updating a second metric comprising a first sub-metric and a second sub-metric indicative of a performance measurement in the second task.

The first sub-metric of the second metric is increased, if the input is received within the second time period at the position of the selectively rendered cue, and/or if the input is absent within the second time period and if no cue was selectively rendered.

The second sub-metric of the second metric is decreased, if the input at the position of the physical object is received within the second time period and if no cue was selectively rendered, and/or if the input is absent within the second time period and the cue was selectively rendered.

The device 100 optionally comprises an initial configuring unit 102 for configuring the HMI by assembling the categories of the plurality of physical objects based on an initial configuration input for each of an extended plurality of physical objects comprising the plurality of physical objects.

The device 100 further optionally comprises a final configuration receiving unit 112 that is configured to receive a final configuration input for each of the plurality of physical objects.

The device 100 still further optionally comprises an initial and final configuration comparing unit 114 that is configured to output a comparison of the initial configuration input and the final configuration input.

Any of the units of the device 100 may be implemented by modules configured to provide the corresponding functionality.

The device 100 may also be referred to as, or may be embodied by, a smartphone, tablet, a transmitting station or a transmitter. The device 100 and a receiver, e.g. an external controller, may be in a radio and/or wired communication at least for the data transmission at the device 100.

Figure 2:
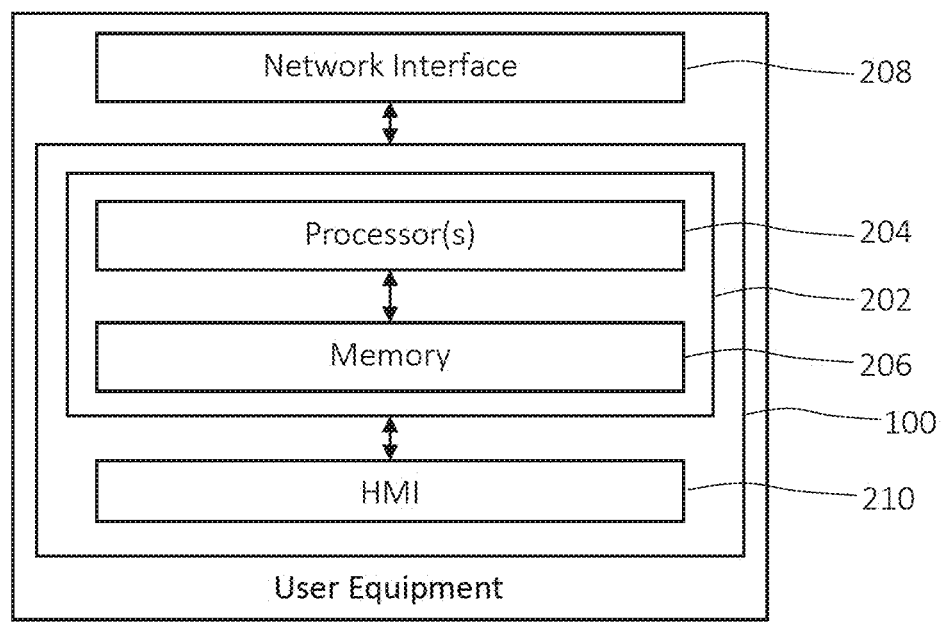
FIG. 2 shows a schematic block diagram of an embodiment of the device of FIG. 1.

FIG. 2 shows a schematic block diagram for an embodiment of the device 100 comprising an HMI 210.

The device 100 comprises processing circuitry 202 comprising one or more processors 204 for performing the method 400 (detailed below in connection with FIGS. 4A, 4B and 4C) and memory 206 coupled to the processor(s) 204. For example, the memory 206 may be encoded with instructions that implement at least one of the units 104, 106, 108 and 110.

The one or more processors 204 may be a combination of one or more of a microprocessor, controller, microcontroller, central processing unit, digital signal processor, application specific integrated circuit, field programmable gate array, or any other suitable computing device, resource, or combination of hardware, microcode and/or encoded logic operable to provide, either alone or in conjunction with other components of the device 100, such as the memory 206, HMI 210 controlling functionality. For example, the one or more processors 204 may execute instructions stored in the memory 206. Such functionality may include providing various features and steps discussed herein, including any of the benefits disclosed herein. The expression "the device being operative to perform an action" may denote the device 100 being configured to perform the action.

As schematically illustrated in FIG. 2, the device 100 may be embodied by a user equipment (UE) 200, e.g., functioning as a radio device in a wireless communication system and/or a device in a wired communication system. The UE 200 comprises a network (e.g., radio) interface 208 coupled to the device 100 for (e.g., radio and/or wired) communication with, e.g., an external controller (not shown in FIG. 2).

Each of the device 100 and the device 200 may be a radio device. Herein, any radio device may be a mobile or portable station (e.g., a smartphone or tablet computer) and/or any radio device wirelessly connectable to a base station or RAN, or to another radio device. A radio device may be a user equipment (UE). Two or more radio devices may be configured to wirelessly connect to each other, e.g., in an ad hoc radio network or via a 3GPP sidelink connection. Furthermore, any base station (e.g., embodying and/or connecting to an external controller) may be a station providing radio access, may be part of a radio access network (RAN) and/or may be a node connected to the RAN for controlling radio access. Further a base station may be an access point, for example a Wi-Fi access point.

Figure 3:
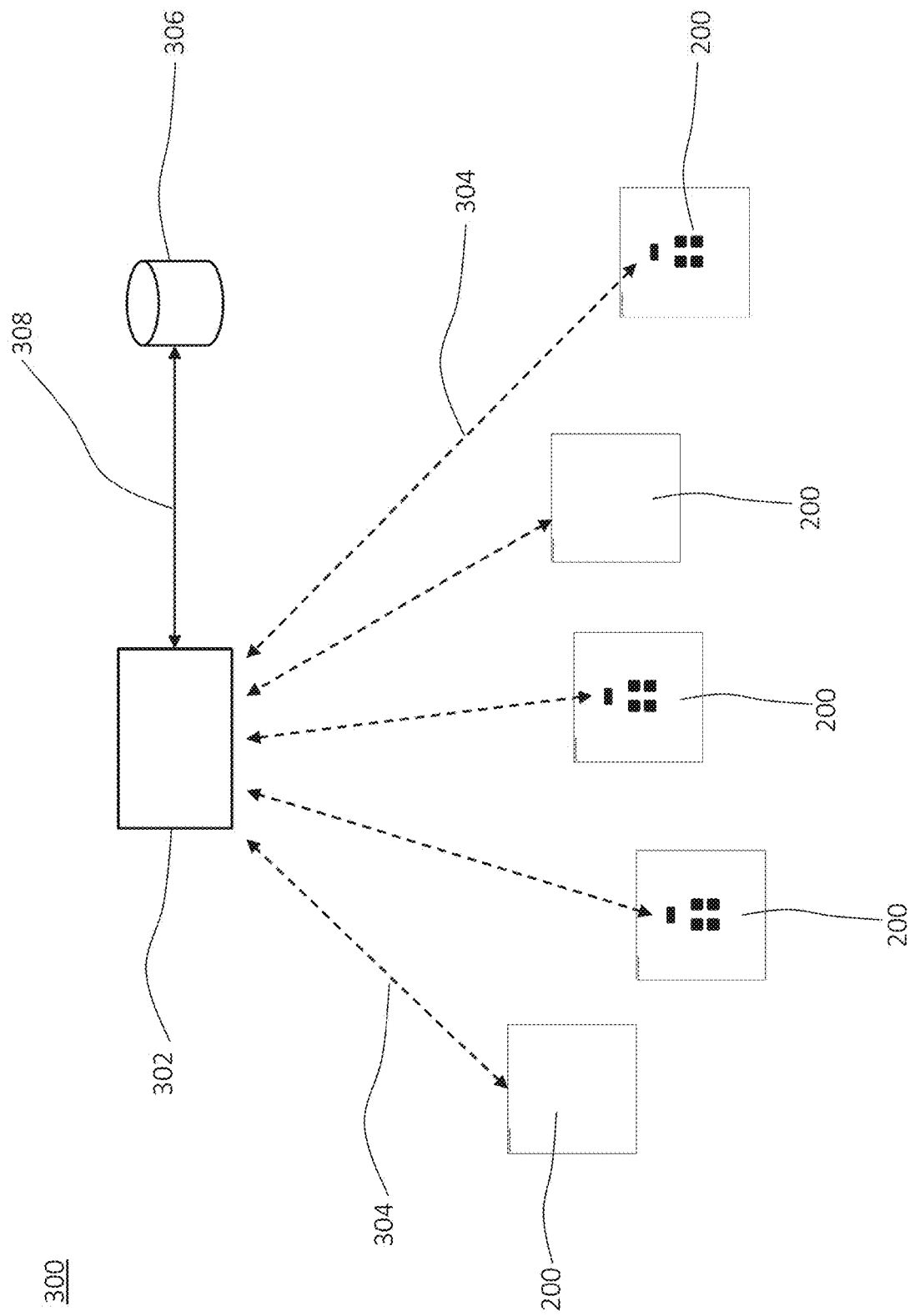
FIG. 3 shows a schematic diagram of an embodiment of a system for controlling an HMI comprising a plurality of devices, an external controller and a storage server, with each of the devices implementable by the device of FIG. 1 and/or FIG. 2.

With reference to FIG. 3, in accordance with an embodiment, a system 300 for controlling an HMI comprises a plurality of devices 200 (e.g., embodied by smartphones and/or tablet computers) and/or an external controller 302 and/or a storage server 306. The external controller 302 may be configured for data communication 304 (e.g., at the start and/or at the end of each session, run and/or day of controlling the HMI for the first task and/or at the start and/or at the end of each session, run and/or day of controlling the HMI for the second task) with each of the devices 200 for receiving the respective updates of the first metric and the second metric and optionally for triggering a notification to one or more of the devices 200. The storage server 306 may be configured for data communication 308 with the external controller 302 and/or for data communication with any of the devices 200 (e.g., through the external controller 302 via data communications 308, 304). Alternatively or in addition, the storage server 306 may be configured for (e.g., direct) data communication (not shown) with any of the devices 200.

The data communication 304 between the external controller 302 and any of the devices 200 and/or the data communication 308 between the storage server 306 and the external server 302 and/or any of the devices 200 may comprise a radio communication within a telecommunication network, such as a 3GPP-type cellular network, which comprises a plurality of base stations (e.g., for connecting to and/or embodying the external controller 302), such as NBs, eNBs, gNBs or other types of wireless access points, each defining a corresponding coverage area. Each base station is connectable to a core network (e.g., for connecting to the storage server 306) over a wired or wireless connection.

While a plurality of devices 200 are illustrated in the example system 300 of FIG. 3, the disclosed embodiments are equally applicable to a situation where a sole device 200 is in the coverage area or where a sole device 200 is connecting to the external controller 302.

The telecommunication network (e.g., comprising and/or connecting to the external controller 302) itself may be connected to a host computer (e.g., comprising the storage server 306), which may be embodied in the hardware and/or software of a standalone server, a cloud-implemented server, a distributed server or as processing resources in a server farm. The host computer (e.g., comprising the storage server 306) may be under the ownership or control of a service provider, or may be operated by the service provider or on behalf of the service provider. The connections (e.g., the connection 308) between the telecommunication network (e.g., comprising the external controller 302) and the host computer (e.g., comprising the storage server 306) may extend directly from the core network to the host computer (e.g., comprising the storage server 306) or may go via an optional intermediate network (not shown in FIG. 3). The intermediate network may be one of, or a combination of more than one of, a public, private or hosted network; the intermediate network, if any, may be a backbone network or the Internet; in particular, the intermediate network may comprise two or more sub-networks (not shown).

The system 300 of FIG. 3 as a whole enables connectivity between one of the connected devices 200 and the host computer (e.g., comprising the storage server 306). The connectivity may be described as an over-the-top (OTT) connection (not shown). The host computer (e.g., comprising the storage server 306) and the connected devices 200 are configured to communicate data and/or signaling via the OTT connection, using an access network, the core network, any intermediate network and/or possible further infrastructure (not shown) as intermediaries. The OTT connection may be transparent in the sense that the participating communication devices through which the OTT connection passes are unaware of routing of uplink and downlink communications. For example, a base station (e.g., comprising and/or functioning as external controller 302) need not be informed about the past routing of an incoming downlink communication with data originating from the host computer (e.g., comprising and/or connected to the storage server 306) to be forwarded (e.g., handed over) to a connected device 200. Similarly, the base station (e.g., comprising and/or functioning as external controller 302) need not be aware of the future routing of an outgoing uplink communication originating from the device 200 towards the host computer (e.g., comprising and/or connected to the storage server 306).

Figure 4A:
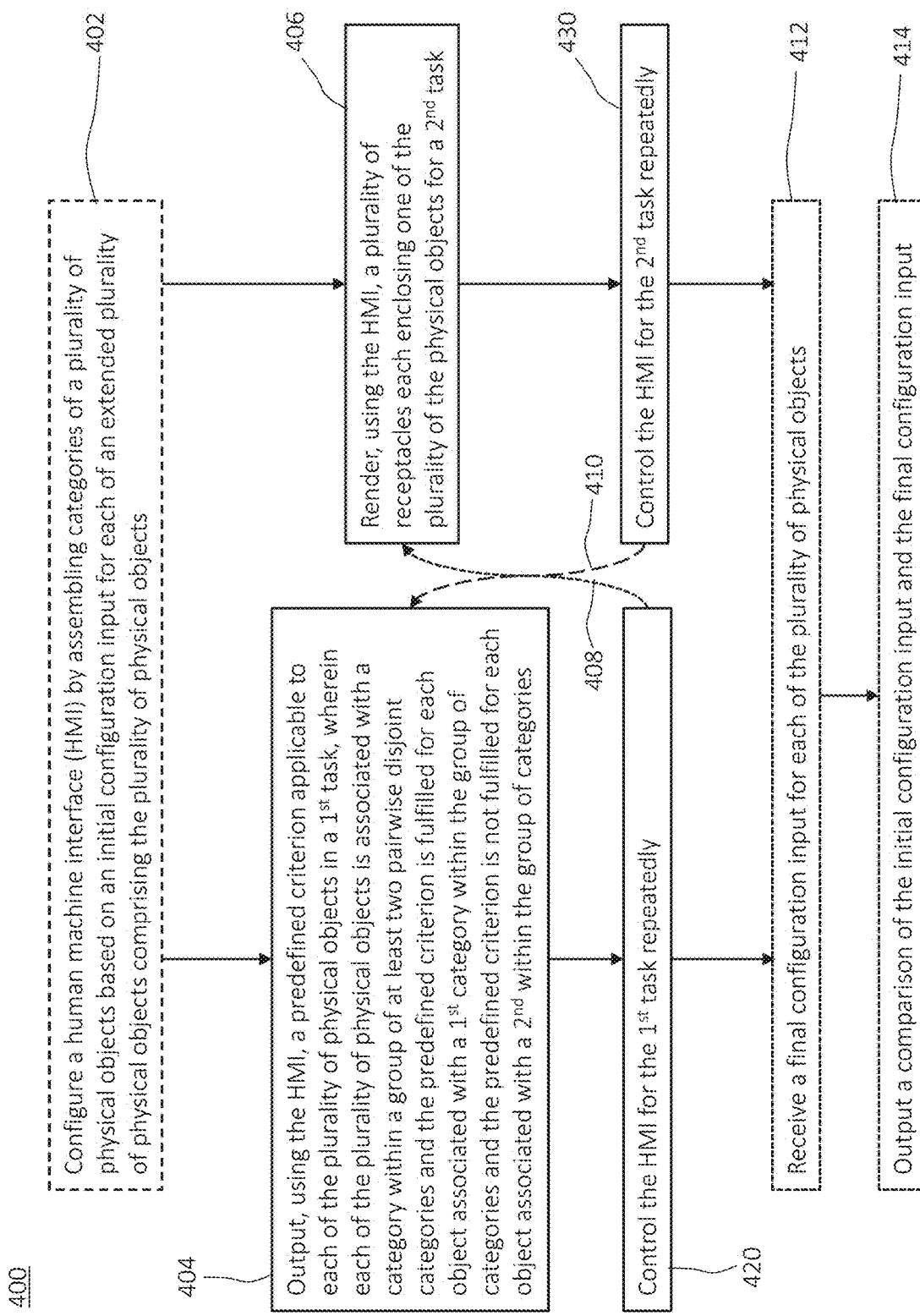
FIGS. 4A to 4C show schematic flowchart of an implementation of a method of controlling an HMI for a first task and for a second task, which method may be implementable by the device of FIG. 1 and/or FIG. 2.
Figure 4B:
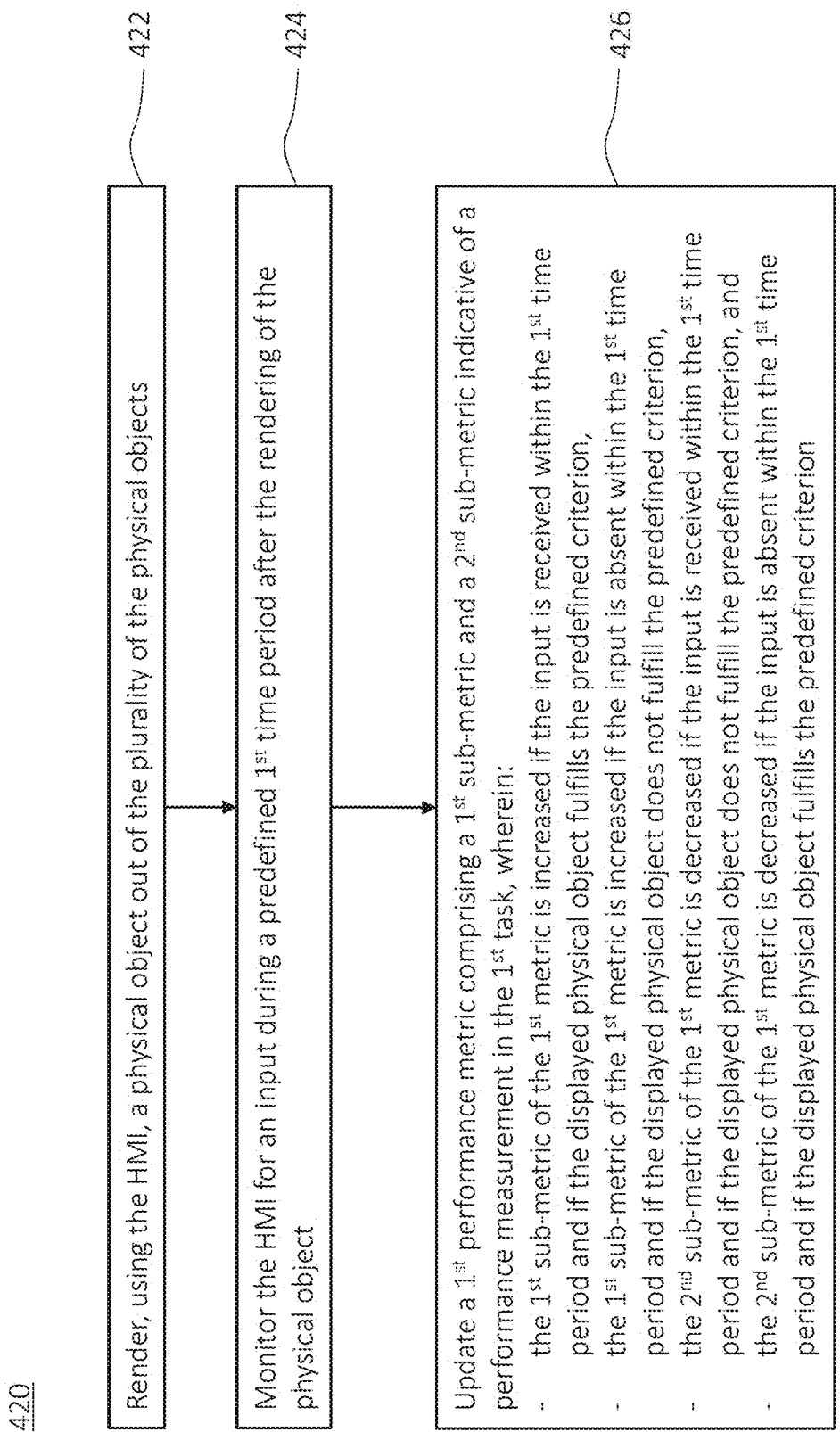
Figure 4C:
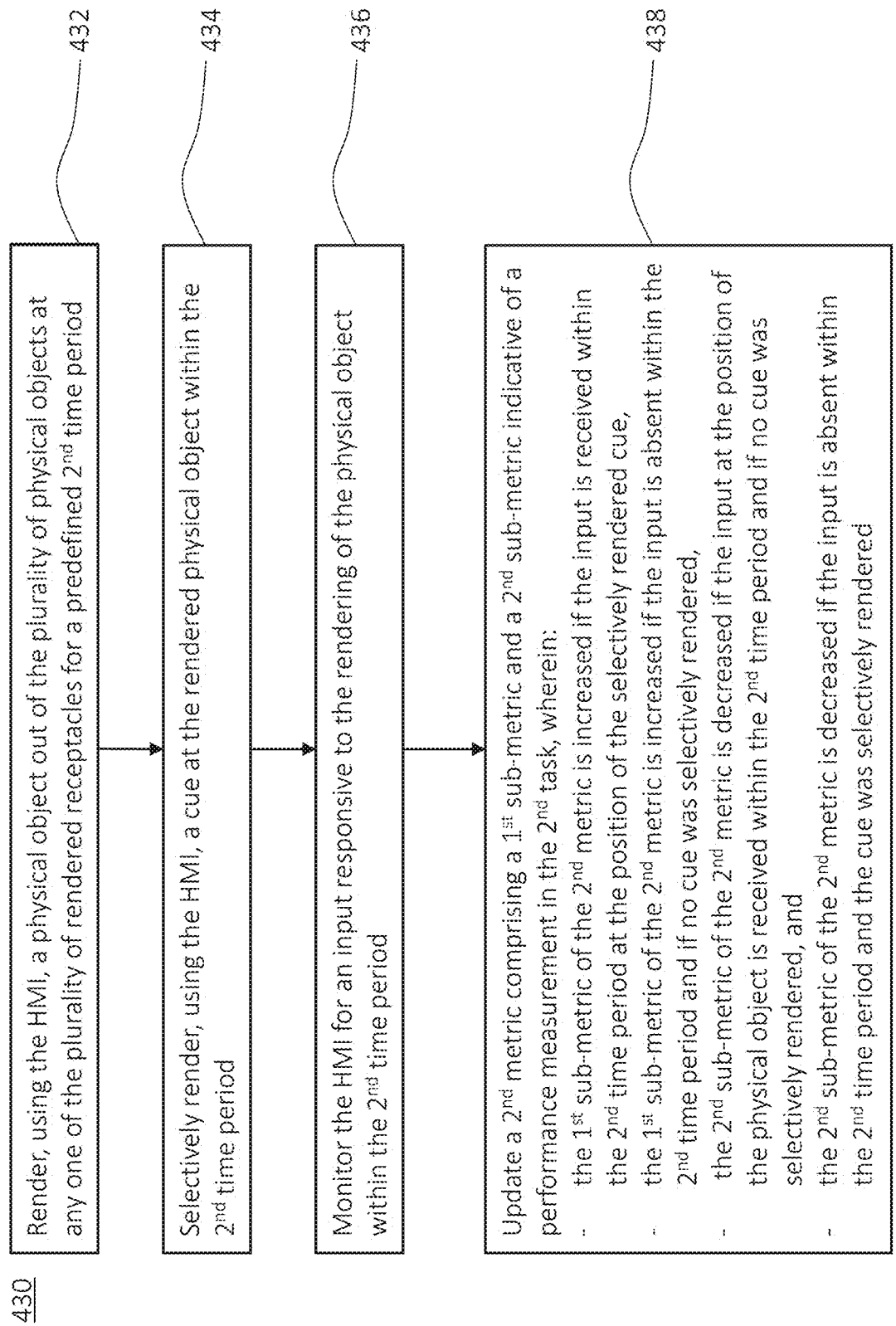

FIGS. 4A, 4B, and 4C show an example flowchart for a method 400 of controlling an HMI. The method 400 comprises or initiates a step 404 of outputting, using the HMI, a predefined criterion applicable to each of a plurality of physical objects in a first task. Each of the plurality of physical objects is associated with a category within a group of at least two pairwise disjoint categories. The predefined criterion is fulfilled for each physical object associated with a first category within the group of categories. Alternatively or in addition, the predefined criterion is not fulfilled for each physical object associated with a second category within the group of categories.

The method 400 further comprises or initiates a series of repeatedly performed steps for controlling the HMI for the first task. The series of steps is generally referred to by reference sign 420 in FIG. 4A.

With reference to FIG. 4B, the series 420 of repeatedly performed steps for controlling the HMI for the first task comprises a step 422 of rendering, using the HMI, a physical object out of the plurality of physical objects. The series 420 further comprises a step 424 of monitoring the HMI for an input during a predefined first time period after rendering the physical object. The series 420 still further comprises a step 426 of updating a first metric comprising a first sub-metric and a second sub-metric indicative of a performance measurement in the first task.

The first sub-metric of the first metric is increased if the input is received within the first time period and if the displayed physical object fulfills the predefined criterion. The first sub-metric of the first metric is also increased if the input is absent within the first time period and if the displayed physical object does not fulfill the predefined criterion.

The second sub-metric of the first metric is decreased if the input is received within the first time period and if the displayed physical object does not fulfill the predefined criterion. The second sub-metric of the first metric is also decreased if the input is absent within the first time period and if the displayed physical object fulfills the predefined criterion.

With reference to FIG. 4A, the method 400 further comprises or initiates a step 406 of rendering, using the HMI, a plurality of receptacles each enclosing one of the plurality of physical objects for a second task.

The method 400 further comprises or initiates a series of repeatedly performed steps for controlling the HMI for the second task. The series of steps is generally referred to by reference sign 430 in FIG. 4A.

With reference to FIG. 4C, the series 430 of repeatedly performed steps for controlling the HMI for the second task comprises a step 432 of rendering a physical object out of the plurality of physical objects at any one of the receptacles for a predefined second time period. The series 430 further comprises a step 434 of selectively rendering, using the HMI, a cue at the rendered physical object within the second time period. The series 430 still further comprises a step 436 of monitoring the HMI for an input responsive to rendering the physical object within the second time period. The series 430 even further comprises a step 438 of updating a second metric comprising a first sub-metric and a second sub-metric indicative of a performance measurement in the second task.

The first sub-metric of the second metric is increased if the input is received within the second time period at the position of the selectively rendered cue. The first sub-metric of the second metric is also increased if the input is absent within the second time period and if no cue was selectively rendered.

The second sub-metric of the second metric is decreased if the input at the position of the physical object is received within the second time period and if no cue was selectively rendered. The second sub-metric of the second metric is also decreased if the input is absent within the second time period and the cue was selectively rendered.

With reference to FIG. 4A, the controlling 420 of the first task and the controlling 430 of the second task may be linked as schematically shown at reference signs 408 and 410.

For example, by the update of the first sub-metric of the first task, the second sub-metric of the second task may be modified at reference sign 408 (e.g., for a following session, run and/or day or any dedicated respective predefined time period). Alternatively or in addition, by the update of the first sub-metric of the second task, the second sub-metric of the first task may be modified at reference sign 410 (e.g., for a following session, run and/or day or any dedicated respective predefined time period).

The first sub-metric of the first metric and/or of the second metric may, e.g., comprise a score (e.g., as a sub-sub-metric). The second sub-metric of the respective metric may, e.g., comprise two gauges for accuracy and speed (e.g., as sub-sub-metrics). By lowering the score achieved in one task, any one or both of the two gauges of the other task may be modified, e.g., a predetermined maximum or initial filling state may be increased, and/or a gauge may be periodically refilled (e.g., for or after a predefined time period and/or within a run, session and/or day).

The method 400 optionally comprises a step 402 of configuring the HMI by assembling the categories of the plurality of physical objects based on an initial configuration input for each of an extended plurality of physical objects comprising the plurality of physical objects. The step 402 may be performed once at the beginning of controlling the HMI for the first task and/or the second task. For example, the step 402 may be performed on the first day and/or at the beginning of the first run and/or session.

The method 400 further optionally comprises a step 412 of receiving a final configuration input for each of the plurality of physical objects. The step 412 may, e.g., be performed at the end or after a predefined number of days and/or weeks (e.g., 20 workdays or four weeks) of controlling the HMI for the first task and for the second task.

The method 400 still further optionally comprises a step 414 of outputting a comparison of the initial configuration input and the final configuration input. By the comparison, e.g., an effectiveness of the controlling of the HMI may be determined.

The method 400 may be performed by the device 100. For example, the units 102, 104, 106, 108, 110, 112 and 114 may perform the steps 402, 404, 420, 406, 430, 412 and 414, respectively.

By combining the controlling of the HMI for the first task and for the second task in the method 400, a cognitive training of a user of the HMI may be performed. The cognitive training may be personalized and/or individualized by the step 402 of configuring the HMI. For example, the plurality of physical objects used for rendering in the repeated step 422 of the first task and in the repeated step 432 of the second task may be selected from an extended plurality of physical objects depending on a direction and/or a goal of the cognitive training (e.g., in terms of modifying a subconscious preference and/or valuation).

For example, the method 400 may be used for the cognitive remediation of neuropsychiatric conditions involving overvaluations of environmental cues.

The step 402 of configuring the HMI may comprise assessing preferences (also denoted as initial configuration input) of the user (e.g., wanting and/or liking dimensions) on an extended plurality of physical objects (also denoted as "environmental cues" or "target items"), e.g., whose consumption should be modulated (e.g., healthy food and/or unhealthy food). The assessment may comprise a range of combined and/or individual methods (e.g., Likert scale, choice task, preference matching algorithm and/or implicit association tests). A ranking of the physical objects within the extended plurality of physical objects may be based on the assessment of preferences. The plurality of physical objects to be rendered in the first task and in the second task may be determined based on the ranking. E.g., the plurality of physical objects may comprise physical objects (e.g., the most and/or least wanted and/or liked) according to the initial configuration input for the controlling of the HMI for the first task and for the second task. The assembly and/or selection of the plurality of physical objects for the first task and for the second task may be based on a distribution of the preference (e.g., relative to a median split) of the extended plurality of physical objects.

Controlling the HMI for the first task and for the second task can provide a (e.g., personalized) cognitive training in view of the plurality of physical objects. For example, reward responses and attentional biases may be advantageously modulated to develop behavior away and/or towards selected (e.g., categories within the plurality of) physical objects by combining repeatedly performing the steps of the first task (also denoted as "Go/NoGo" or "GNG") with repeatedly performing the steps of the second task (also denoted as "Cue Approach Training" or "CAT"). The specificity of the task design (e.g., comprising that each correct input may increase the task difficulty, and/or that after a limited number of errors and/or correct late inputs, the repeatedly performing of steps for the respective task may be terminated and/or interrupted) is also advantageous for the effectiveness of the cognitive training.

Since the overconsumption of, e.g., high-density energy palatable food contributes to the development and maintenance of many health disorders, including obesity, diabetes or metabolic syndrome, cognitive training that reduces this behavior is much needed. Alternative or additional examples leading to the development and maintenance of health disorders comprise the consumption of intoxicants such as nicotine, weed, cigarettes or alcohol.

By performing the first task and the second task of the method of controlling a HMI as disclosed herein, motor response towards physical objects (e.g., food items) are repeatedly inhibited and/or executed. Inhibiting motor responses to one or more categories of physical objects (e.g., energetically dense and palatable food items) during the first task (GNG) can reduce their perceived value, consumption, and a user's weight. Alternatively or in addition, executing motor responses to one or more further task-relevant physical objects (e.g., healthy food items) during the second task (CAT) can induce opposite effects.

Cognitive training in terms of inhibitory control training on (e.g., eating) behavior can reduce (e.g., unhealthy food) consumption by developing 'inhibition reflexes' of the motor responses to the targeted physical objects (also denoted as items, e.g., comprising food items). In the first task (GNG), a user may be instructed to respond as fast as possible to one or more given categories of physical objects (e.g., food items) and to withhold a response to one or more further categories. Such a first task can act as motivational conditioning paradigm which can automatize the engagement of inhibition processes via associative learning mechanisms and reduce the perceived value of physical objects (also denoted as "NoGo stimulus") from one or more categories for which the response is to be withheld. When a NoGo stimulus becomes associated with avoidance and/or aversion, its presentation can directly trigger the avoidance and/or aversive center, which can suppress the activation of the approach and/or appetitive center. This mechanism can decrease the hedonic and motivational value of the NoGo stimuli.

Cognitive training in terms of approach bias training can modulate a valuation of a physical object (e.g., food item) by developing attentional and approach biases towards (e.g., healthy food) cues. In the second task (CAT), physical objects (e.g., food items) are displayed for a short period during which a Go-cue prompting a motor response may selectively be presented. The task of the user is to respond to cued physical objects before their offsets and/or before their vanishing (e.g., within the predefined second time period). Since task performance can be improved by paying attention to and rapidly reaching the physical objects associated with the cues (but not to those not associated with the cue), attention and approach tendency can be automatically allocated to the cued items. The target items saliency and valuation (also denoted as "perceived value") can increase as well as their consumption.

Responses to Go stimuli during the first task (GNG) and the withholding of responses to the non-cued stimuli during the second task (CAT) can (e.g., respectively) develop approach and/or avoidance tendency.

The development of automatic inhibition to one or more categories of physical objects (e.g., unhealthy food items) and of attentional biases towards one or more further categories of physical objects (e.g., healthy food items) can act synergistically to improve cognitive skills and/or behavior (e.g., eating habits). The method 400 disclosed herein can promote the replacement of one or more categories of physical objects (e.g., unhealthy food items) by one or more further categories of physical objects (e.g., healthy food items) and not merely reducing the consumption of the one or more categories of physical objects (e.g., unhealthy food item consumption), thereby ensuring to maintain a cognitive and/or behavioral balance (e.g., satiety). E.g., large decreases of reward responses to unhealthy food items and body fat with multifaceted training approach involving both attentional bias modification and response inhibition approaches can be achieved.

By the method 400, a double-blind, placebo-controlled, parallel, randomized cognitive training can be performed for a predefined time, e.g. one-month (for example 20 minutes per day, e.g., comprising ten minutes each per GNG and CAT task, five days per week), on the plurality of physical objects (e.g., food items). By the method 400 performed for the predefined time, a valuation of physical objects within one or more categories may decrease (e.g., comprising high-density energy unhealthy food items, for example as indexed by their perceived palatability), and the valuation of physical objects within one or more further categories may increase (e.g., low-density energy healthy food items). Alternatively or in addition, by the method 400, physiological variables of a user may be modified (e.g., the user's food item consumption and/or weight may be reduced).

The controlling of the HMI for the first task (also denoted as GNG task) can reduce the value of physical objects within one or more categories (e.g., unhealthy food items) by associating them with motoric inhibition. The controlling of the HMI for the second task (also denoted as CAT task) can increase the value of physical objects within one or more further categories e.g., healthy food items) by biasing attention and approach tendency toward them.

Embodiments of the technique can maximize motivation and adherence, e.g., by an advantageous auditory and visual (e.g., audiovisual) task controlling environment, intrinsic and social challenge and/or mechanisms to increase any one of the first metric and the second metric, or any sub-metric thereof. Alternatively or in addition, progressive difficulty levels enable that the controlling of the first task and of the second task remain adapted to a user's performance (e.g., an improvement thereof).

Further alternatively or in addition, the controlling of the HMI for the first task and for the second task can be personalized and/or individualized to a (e.g., each) user's needs (e.g., tastes and/or eating habits) by specifically targeting their preferred physical objects (e.g., high-density energy items), as measured with (e.g., palatability) scales at the beginning (e.g., for the first time) of the controlling of the HMI.

The optional step 402 of initially configuring the HMI and/or the optional step 412 of a final configuration will now be described in connection with FIG. 5.

Figure 5:
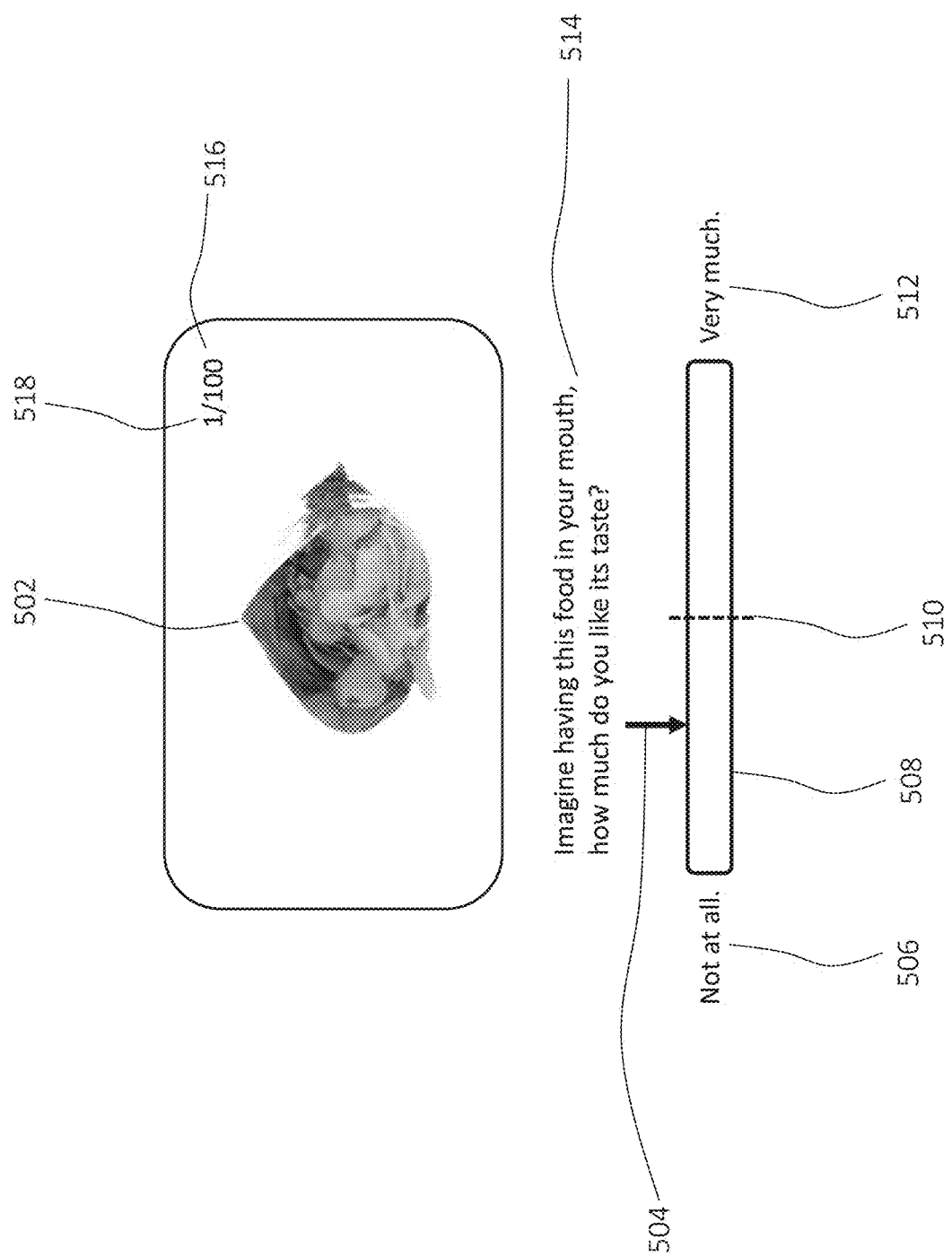
FIG. 5 schematically illustrates an example diagram of assessing physical objects in an initial configuration step, which may correspond to an embodiment of the first optional step 402 of the method of FIG. 4A.

In FIG. 5, an analogue scale 508 is used to assess the perception of a (e.g., extended) plurality of physical objects 502 before and/or after repeatedly controlling the HMI for the first task and for the second task for a predefined total time (e.g., on the first day and/or on the last day of the controlling of the HMI with the predefined total time, e.g., comprising four weeks).

A total number comprised in the (e.g., for the step 402 extended) plurality of physical objects (e.g., one hundred in total with counting the first of them displayed at reference sign 518) is displayed at reference sign 516. The plurality of physical objects 502 may be divided into one or more categories sharing a feature (e.g., one or more categories comprising fifty healthy food items and/or one or more categories comprising fifty unhealthy food items).

Figure 6:
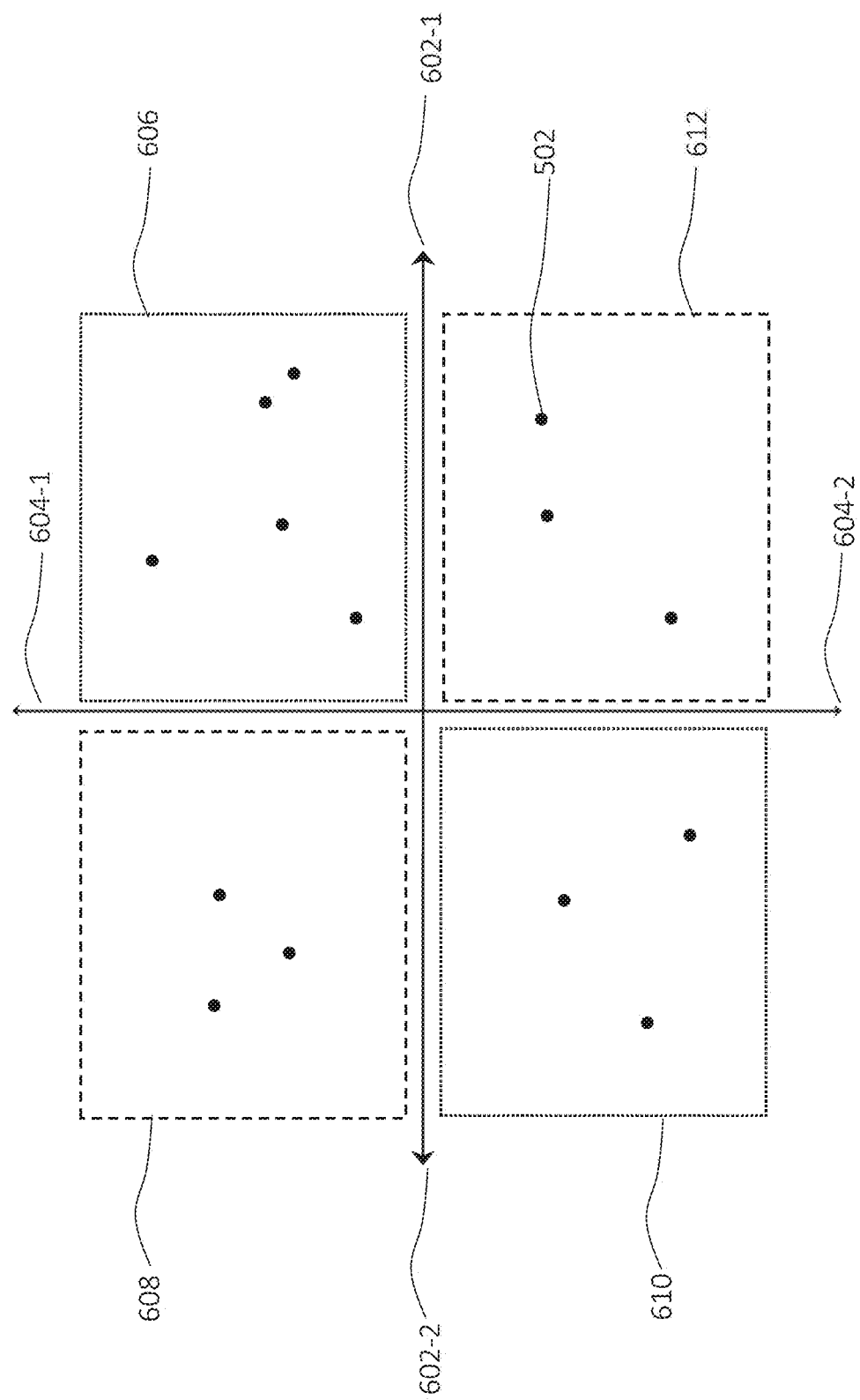
FIG. 6 schematically illustrates a schematic diagram of associating physical objects to four pairwise disjoint categories comprised in a group of categories, with each category associated to a combination of two exemplary mutually orthogonal features.

As shown in FIG. 6, a category within a group of pairwise disjoint categories may comprise physical objects 502 sharing two or more features. In FIG. 6, at reference sign 602-1 a grade of a physical object 502 having a first feature (e.g., a food item being "healthy") and at reference sign 602-2 a grade of the physical object 502 not having the first feature (e.g., a food item being "unhealthy") are displayed. On an, e.g., orthogonal scale, at reference sign 604-1 a grade of the physical object 502 having a second feature (e.g., a food item being "sweet") and at reference sign 604-2 a grade of the physical object 502 not having the second feature (e.g., a food item being "salty" instead of "sweet") is displayed.

By combining two features, the plurality of physical objects 502 in FIG. 6 is grouped into four pairwise disjoint categories at reference signs 606, 608, 610 and 612 (e.g., comprising food items labelled as "healthy and sweet", "unhealthy and sweet", "unhealthy and salty" and "healthy and salty", respectively).

In the initial configuration step 402 and/or in the final configuration step 412 of the method 400, the physical objects 502 are rendered (also: "displayed" as exemplified in FIG. 5 by a photo of a physical object) sequentially at the HMI (e.g., on a screen of a tablet computer and/or smartphone) in a randomized order, along with a question concerning its preference and/or assessment by a user (e.g., "Imagine having this food in your mouth, how much do you like its taste?" at reference sign 514). The user may report his/her preference (also: assessment or rating) on the (e.g., ten centimeter, 10 cm, long) analogue scale 508 ranging from "not at all" at reference sign 504 to "very much" at reference sign 512, e.g. as minimal-maximal anchors (e.g., respectively 0 and 100 points on the scale 508), and optionally with a marker in the middle (e.g., at 50 points) at reference sign 510. The marker 510 in the middle of the scale 508 may correspond to the assessment of the physical object being neutral.

An indicator (e.g., arrow) at reference sign 504 indicates the user's assessment and/or level of preference (e.g., where he/she has responded on the scale 508).

In the step 402 of the initial configuration, the physical objects 502 displayed may be comprised in an extended plurality of physical objects 502. Alternatively or in addition, the plurality of physical objects 502 rendered in the repeated steps 422 and 432 of the first task and of the second task, respectively, may comprise a sub-plurality of the extended plurality of physical objects 502 sequentially rendered in a randomized order in the step 402 of initially configuring the HMI.

In the step 412 of receiving a final configuration, only a sub-plurality of physical objects 502 of the extended plurality of the initial configuration step 402 may be rendered. E.g., only physical objects 502, which were initially assessed at and/or above a median split (e.g., determined from a distribution of the initial assessment of the extended plurality of physical objects 502) in the step 402, may be rendered in the step 412. Alternatively or in addition, the plurality of physical objects 502 rendered in the step 412 may be comprised in or may correspond to the plurality of physical object 502 repeatedly rendered in the steps 422 and 432 of the first task and of the second task, respectively.

The total number of sequentially rendered physical objects 502 at reference sign 516 in FIG. 5 may be larger for the initial configuration step 402 than for the final configuration step 412.

By determining, e.g., a median split in the initial configuration step 402, the extended plurality of physical objects 502 may be reduced to the plurality of physical objects 502 available and/or used for rendering in the repeatedly performing steps 422 and 432 of the first task and of the second task, respectively, and/or of the final configuration step 412.

In any step of rendering physical objects 502 (e.g., the steps 402 and 412 of initial configuration and final configuration, respectively, as well as the repeatedly performed steps 422 and 432 of the first task and of the second task, respectively), physical objects 502, a feature of which is classified as "neutral" (e.g., neither "healthy" nor "unhealthy"), may be rendered (e.g., at randomized points in a sequence and/or in time) as distractors. Such "neutral" distractor physical objects 502 may be exempt from any evaluation performed in the steps 402, 412 and/or 414 of initial configuration, final configuration and/or comparing the initial and the final configurations, respectively.

To improve the sensitivity of the assessment and/or ratings of the physical objects 502 to devaluation effects, a user may be instructed to assess and/or rate each physical object 502 intuitively and to complete the sequence of assessments (also denoted as "questionnaires") at a predefined moment in time (e.g., just after reporting a user-specific physiological value such as his/her weight). The predefined moment in time may comprise a predefined time of the day and/or of a user-specific daily rhythm, e.g. after waking up and/or before eating (for example before breakfast).

The physical objects 502 (also denoted as "stimuli") may comprise images and/or photos, e.g., of food items selected from an existing database, e.g. the "Food-Pics" database published by J. Blechert et al. in "Food-pics: an image database for experimental research on eating and appetite," Front. Psychol., vol. 5, p. 617, June 2014, doi: 10.3389/fpsyg.2014.00617. Alternatively or in addition, the physical objects 502 may comprise images and/or photos of, e.g., food items selected from freely available images and/or photos on the Internet. The images and/or photos of food items may be divided into, e.g., six categories based on their healthiness ("healthy", "unhealthy" and/or "neutral") and on their sweetness ("sweet" and/or "salty"). Healthy food items may be defined as having a caloric density below the first quartile of the food picture database (e.g., <49.9 kcal/100 g and/or a caloric density below fifty kilocalories per one hundred gram food). Alternatively or in addition, unhealthy food items may be defined by being above the median (e.g., >198 kcal/100 g and/or above a caloric density of two hundred kilocalories per one hundred gram food). Further alternatively or in addition, food items may be considered as "neutral" when they could not or should not be qualified as either healthy or unhealthy (e.g., rice), if their eaten quantity may be a major factor determining their healthiness (e.g., red meat, and/or spices such as salt, sugar, honey and/or maple syrup, which are conventionally consumed in minuscule amounts) or if their image and/or photo includes both healthy and unhealthy food components (e.g., pancake with fruit pieces).

A database comprising the extended plurality of physical objects 502 may be compiled and/or augmented based on the specific purpose and/or goal of the cognitive training. E.g., a standardized database of food items such as a database comprising the "Food-Pics" database may be augmented by images and/or photos of crisps, salt, sugar, chocolate bars, soda, salad fruit and/or milkshakes. Alternatively or in addition, based on the data from the "Food-Pics" database, the selected (e.g., for the extended plurality of physical objects 502 in the configuring step 402) healthy food items and unhealthy food items may, e.g., have mean palatability ratings of, respectively, 60.2 and 62.3 on a scale 508 ranging from 0 to 100 (e.g., corresponding to a statistical effect size of Cohen's d=0.23).

The repeatedly performed steps 422, 424 and 426 of the first task and the repeatedly performed steps 432, 434, 436 and 438 of the second task will now be exemplarily described in connection with FIG. 7 and FIG. 8, respectively.

The method 400 of controlling the HMI may be implemented as a mobile operating system, e.g., an android application such as developed on the 2019 version of Unity software (Unity3d.com, 2015).

Before starting a run and/or session (e.g., a sequence of repeatedly performing the steps 422 to 426 of the first task and/or the steps 432 to 438 of the second task), a user may be able to freely choose between the first task (GNG) and the second task (CAT). The same principle may apply to each of the first task and the second task. A user may have to consecutively (e.g., in a row) repeat the steps of the respective task as often as possible, e.g. until a gauge representing the respective second sub-metric reaches a predefined minimum. The consecutive repetitions of the steps of the respective task may also be denoted as a "run" and/or "session".

Each correct input and/or correct non-input (collectively denoted as "successful trial" and/or "correct trial") may increase the first sub-metric of the respective metric, e.g. comprising a difficulty level (briefly: "level"), which may be increased after a predefined number (e.g., five or six) of successful trials. Alternatively or in addition, the first sub-metric of the respective metric may comprise a score, which is increased after each successful trial. The amount of increase in the score may be based on the difficulty level. Further alternatively or in addition, the consecutive repetitions of the steps of the respective task, "run" and/or a "session" may be terminated after a predefined number of incorrect inputs, incorrect non-inputs and/or correct late inputs (collectively denotes as "errors"). For example, the second sub-metric of the respective metric of the respective task may comprise two gauges for "accuracy" (also denoted as "correctness") and "speed". The "accuracy" gauge may be decreased by one for every incorrect input and/or every incorrect non-input. The "speed" gauge may be decreased by one for every correct late input. Each gauge may be filled to a predetermined maximum at the beginning of the "run", "session" and/or at the beginning of a day. The "run" and/or "session" may be terminated if at least one of the gauges reaches its predetermined minimum.

Exemplary tasks parameters for the first task and for the second task are reported in table 1.

TABLE 1

Exemplary task-specific parameters

| | First Task (GNG) | Second Task (CAT) |
|---|---|---|
| Go/NoGo rate | 70% Go<br>30% NoGo | 25% Go (cued physical objects)<br>75% NoGo (non-cued physical objects) |
| Stimulus duration<br>Feedback duration | 1.25 second maximum and disappearing after input<br>250 ms | |
| Visual Cue duration | N/A | Until physical object offset |
| Cue delay | N/A | Go Signal Delay (GSD): based on difficulty level, see, e.g., table 3 |
| Interstimulus interval (ISI) | 1000-2000 ms | 800-1300 ms* |

In table 1, the "Go/NoGo rate" corresponds to the percentage of expected correct inputs and the percentage of correct non-inputs, respectively. An expected correct input comprises a physical object fulfilling the predefined criterion for the first task and a cue being selectively rendered for the second task. An expected correct non-input comprises a physical object not fulfilling the predefined criterion for the first task and no cue being selectively rendered for the second task. The "Go/NoGo rate" may be different for the first task and for the second task. For example, the "Go rate" for the first task may be seventy percent (70%). Alternatively or in addition, the "Go rate" for the second task may be twenty-five percent (25%).

The "stimulus duration" in table 1 comprises the predefined first time period for the first task and the predefined second time period for the second task, during each of which a physical object is rendered. The "stimulus duration" may be the same for the first task and for the second task. Alternatively or in addition, the predetermined first time period and the predetermined second time period may be identical. For example, the "stimulus duration" may be maximally 1250 milliseconds (1.25 seconds). The "stimulus duration" may be shortened responsive to a received input.

A "feedback duration" in table 1 may comprise a time period, during which the reception of an input and/or the absence of an input is acknowledged, e.g., by rendering a signal out of a plurality of signals indicative of the input type. For example, the signal may comprise a visual symbol for a correct input and/or correct non-input (e.g., "true"), a correct late input (e.g., "too late") and an incorrect input and/or incorrect non-input (e.g., "false" and/or a cross). Alternatively or in addition, the signal may comprise an audio signal, tune and/or sequence of tunes indicative of the input type. In the example in table 1, the "feedback duration" for the first task and for the second task is identical. Alternatively or in addition, the "feedback duration" may comprise 250 milliseconds (0.25 seconds).

The "visual cue duration" in table 1 comprises the time period during which the cue in the second task may be selectively rendered. For example, the cue may be selectively rendered until the end of the predefined second time period and/or until the rendering of a physical object at one of the receptacles terminates and/or until a rendered physical object disappears.

The "cue delay" (also denoted as "go signal delay" or briefly "GSD") in table 1 comprises the time period from the moment of rendering a physical object in the second task before a cue is selectively rendered. For example, the time (e.g., the instance and/or moment) of rendering the cue may be incrementally delayed as a function of the difficulty level.

The "interstimulus interval" (briefly: "ISI") in table 1 comprises a time period between two repetitions of the repeated steps of the first task and of the second task. The ISI of the second task may shorter than the ISI of the first task. By a shorter ISI, a fatigue and/or boredom may be avoided and/or an effectiveness of the task may be increased, in particular for a low "Go rate", e.g., twenty-five (25%) for the second task.

The percentage of physical objects comprised in at least two pairwise disjoint categories may be variable.

In a first embodiment, in which users are denoted as "experimental group", physical objects may be classified (e.g., may have the feature) as "healthy", "unhealthy" and "neutral" food items with the "Go rate" distributed as displayed in table 2.

A physical object (e.g., food item) with a feature according to table 2 may be comprised in a category. All physical objects within a category may share this feature and at least one further feature. For example, a second feature may comprise a food item being "sweet" or "salty".

A "Go rate" may refer to a rendered physical object fulfilling a predefined criterion. The predefined criterion may, e.g., refer to the at least one further feature. The "Go rate" for one "run" and/or "session" may, e.g., comprise "sweet" food items fulfilling the predefined criterion. For example, a "Go rate" for "sweet" food items may comprise eighty percent (80%) from a category "sweet and healthy" (e.g., water melon) and twenty percent (20%) from a category "sweet and neutral" (e.g., pancake with fruit) in the "experimental group" in table 2.

In a second embodiment, in which users are denoted as "control group", the "Go rate" may comprise physical objects both with and without the feature (e.g., "healthy", "unhealthy" and "neutral"), e.g. a "Go rate" for "sweet" food items may comprise forty percent (40%) each from the categories "sweet and healthy" and "sweet and unhealthy" and twenty percent (20%) from the category "sweet and neutral" in the "control group" in table 2.

TABLE 2

Exemplary embodiments of proportions of physical objects comprised in at least three different category

| Item Type/ Trial Condition | Healthy | Unhealthy | Neutral |
|---|---|---|---|
| Experimental Group | | | |
| Go trials | 80% | 0% | 20% |
| NoGo trials | 0% | 80% | 20% |
| Control Group | | | |
| Go trials | 40% | 40% | 20% |
| NoGo trials | 40% | 40% | 20% |

An example embodiment of the first task (GNG) will now be discussed in connection with FIG. 7.

Figure 7:
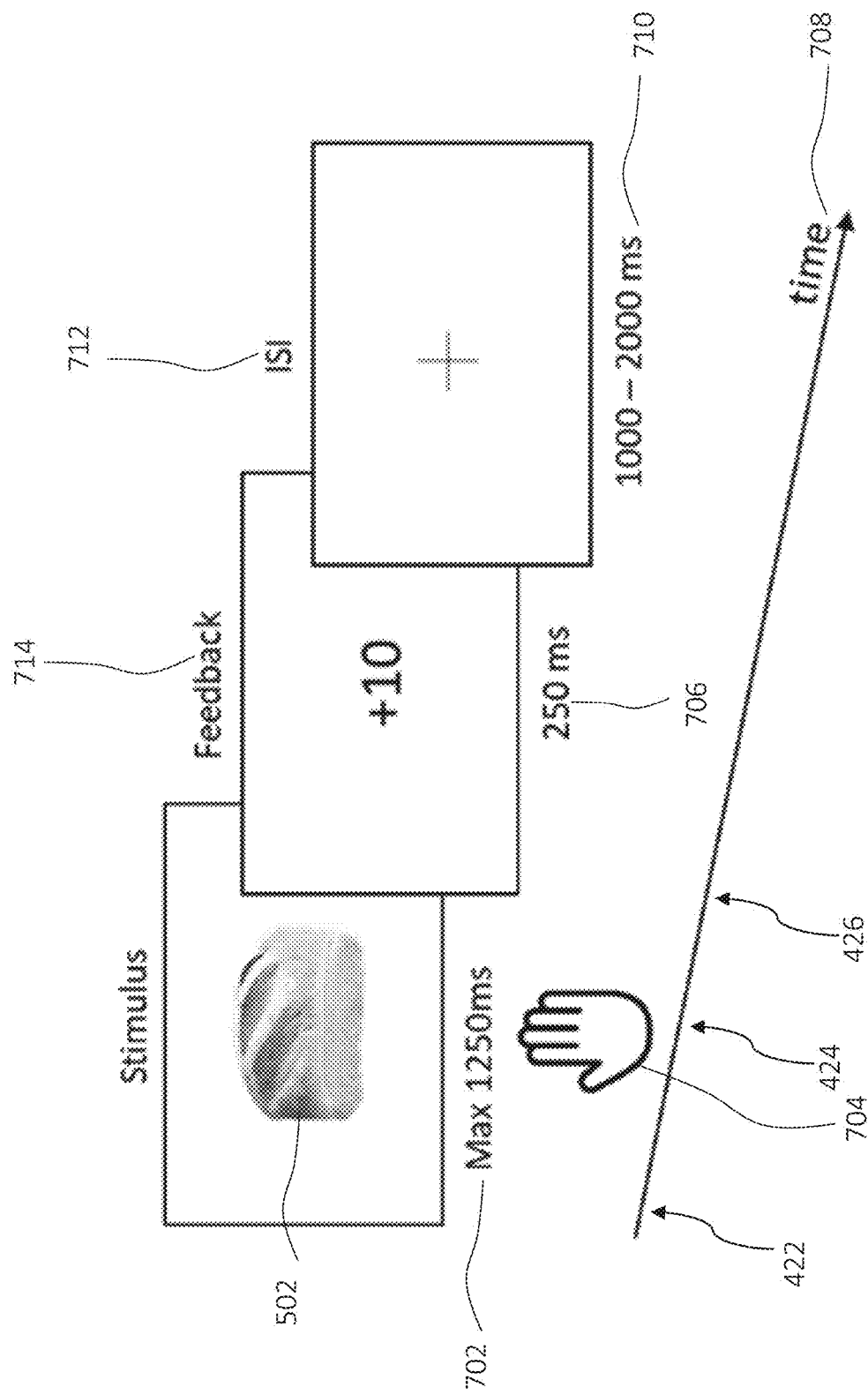
FIG. 7 shows an exemplary timeline for repeatedly performing the first task according to the method steps of FIG. 4B.

In the first task, a physical object 502 is rendered for a predefined first time period, e.g. 1.25 seconds as shown in FIG. 7 at reference sign 702. The scale at reference sign 708 generally shows the progression of time. An input 704 may be received within the predefined first time period. Based on the input 704 or non-input within the predefined first time period, a performance measurement is updated and a feedback (e.g., adding ten points, "+10", to a score comprised in the first sub-metric of the first metric) is rendered at reference sign 714 within the feedback duration 706. The feedback duration 706 may be followed by an ISI at reference sign 712. The ISI may comprise between one and two seconds as shown at reference sign 710. The rendering of the physical object 502, monitoring for an input and update of the first performance metric of the method 400 are exemplified at reference signs 422, 424 and 426, respectively, along the time line 708.

In the first task, as exemplified in FIG. 7, the rendered physical object 502 may comprise an image and/or a photo of a food item. The input may comprise dragging the image within the predefined first time period (e.g., as fast as possible) in a predefined direction (e.g., toward the bottom of a touchscreen of a tablet computer and/or smartphone embodying the HMI) if the physical object 502 in the image and/or photo fulfils the predefined criterion. The predefined criterion for food items may comprise either "sweet" (e.g., orange and/or ice-cream) or "salty" (e.g., green beans and/or hamburger). The predefined criterion may be (e.g., pseudo-randomly and/or with equal distributions of two opposite predefined criteria over a time average) determined and/or output in the method step 404, e.g., at the beginning of a "run" and/or "session".

The presentation of a physical object 502 from any category may be equiprobable and/or pseudo-random.

The predefined first time period may comprise a first time sub-period (also: "Reaction Time Threshold" or briefly "RTT") and a second time sub-period. If an input to a physical object 502 fulfilling the predefined criterion is received within the RTT, a feedback (e.g., "true" and/or a colored visual signal) indicative of a correct input may be rendered. Alternatively or in addition, if the input to the physical object 502 fulfilling the predefined criterion is received after expiry of the RTT but within the second time sub-period of the predefined first time period, a feedback (e.g., "too late") indicative of a correct late input may be rendered.

If a correct input (also: "Hit") is received within the RTT and/or in case of a correct non-input (also: "Correct Rejection" or briefly "CR", e.g., if a physical object 502 rendered does not fulfill the predefined criterion and an input is absent), the rendered feedback may comprise an indication of a change in the first sub-metric of the first performance metric (e.g., a score comprised in the first sub-metric may be increased by a predefined amount).

If an incorrect input (also: "False Alarm" or briefly "FA") is received within the first time period (e.g., within the RTT) and/or in case of an incorrect non-input (also: "Miss", e.g., an input is absent for a rendered physical object 502 fulfilling the predefined criterion), the rendered feedback (e.g., "false" and/or a, typically colored for example in red, cross) may comprise an indication of the second sub-metric of the first metric being decreased (e.g., an "accuracy" gauge comprised in the second sub-metric may be decreased by one).

Alternatively or in addition, if a correct late input is received, the feedback may comprise an indication of the second sub-metric of the first metric being decreased (e.g., a "speed" gauge comprised in the second sub-metric may be decreased by one).

There may be seventy percent (70%) of Go trials and thirty (30%) of NoGo trials to influence a response potency of the cognitive training.

The feedback on performance may interact with the effect of cognitive training. Alternatively or in addition, the feedback allows to ensure a correct understanding of the instructions by the user and/or using "scores" as performance parameters.

In the following, an embodiment of the second task (CAT) is described in connection with FIG. 8.

In the second task, physical objects 502 (e.g., food items) are (e.g., sequentially) rendered (e.g., on a touchscreen of a tablet computer and/or smartphone embodying the HMI) at one of a plurality of predefined locations. The plurality of predefined locations may comprise a plurality of receptacles (e.g., cardboard boxes).

Figure 8:
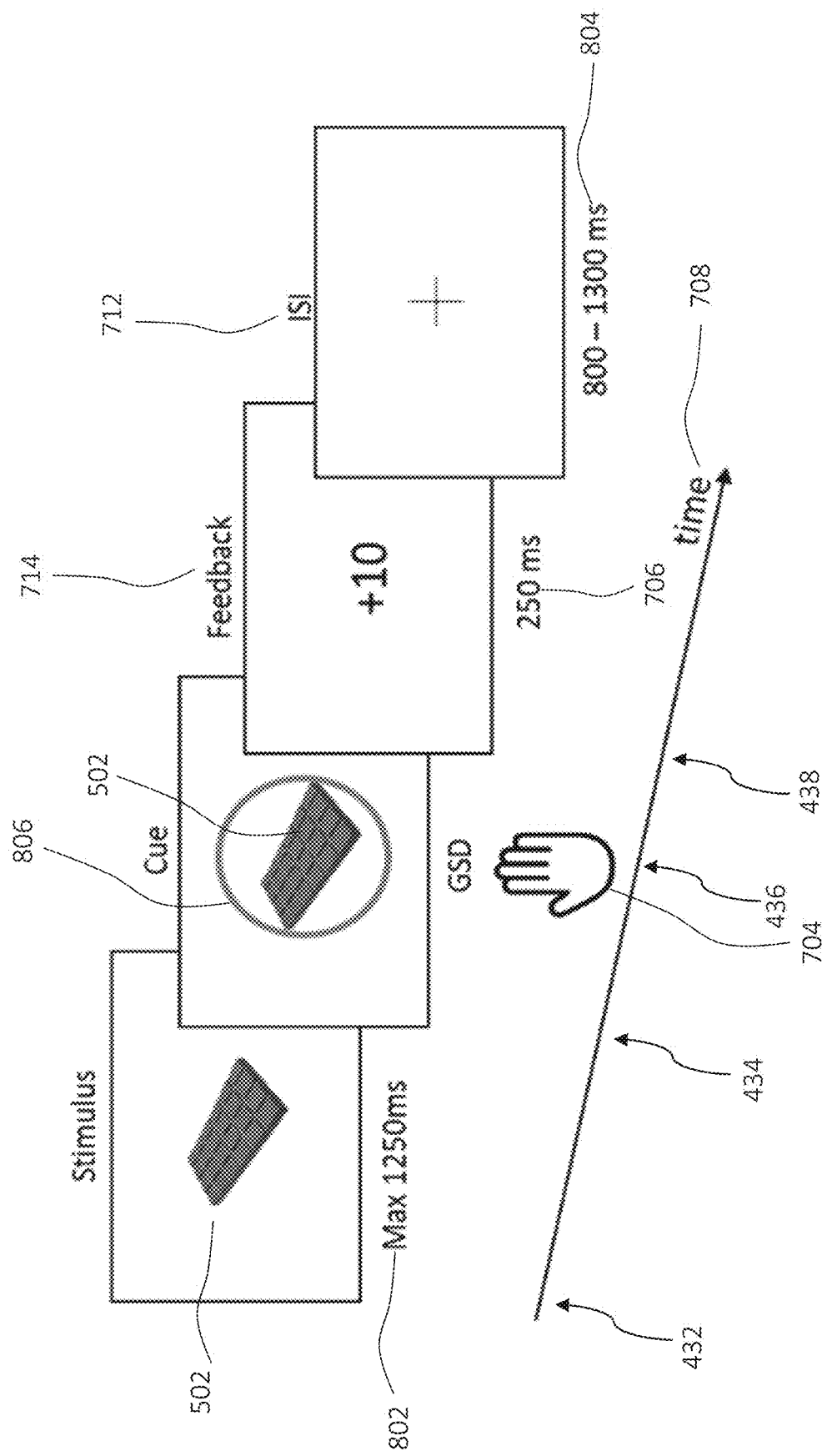
FIG. 8 shows an exemplary timeline for repeatedly performing the second task according to the method steps of FIG. 4C.

A user may be instructed to provide an input 704 for the second task only receptive to a selectively rendered cue 806 (e.g., a green circle around the physical object 502 and/or a bell sound) during a predefined second time period, e.g., 1.25 seconds at reference sign 802 in FIG. 8. The rendering of the physical object 502 may be stopped after expiry of the predefined second time period 802.

In case of a correct input (also: "Hit") received within a first time sub-period of the predefined second time period 802, a feedback 714 (e.g., "true") displayed during a feedback duration 706 (e.g., of 0.25 seconds) may comprise an increase in the first sub-metric of the second performance metric (e.g., an increase by ten, "+10", points of a score comprised in the first sub-metric of the second metric). Alternatively or in addition, the feedback may comprise an increase in a difficulty level after a predefined number (e.g., five or six) correct inputs.

In case of a correct late input within a second time sub-period and/or within a predefined time period consecutive to the predefined second time period 802, the feedback 714 (e.g., "too late") may comprise a decrease in the second sub-metric of the second metric (e.g., a decrease in a "speed" gauge by one).

In case of an incorrect input (also: "FA") and/or an incorrect non-input (also: "Miss") within the predefined second time period 802, the feedback 714 (e.g., "false" and/or a, typically colored for example in red, cross) may comprise a decrease in the second sub-metric of the second metric (e.g., a decrease in an "accuracy" gauge by one).

In case of a correct non-input (e.g., a CR, i.e., the correct rejection) within the predefined second time period 802, the feedback 714 (e.g., "true") may comprise an increase in the first sub-metric of the second performance metric (e.g., an increase in a score comprise in the first sub-metric).

The increase in the score caused by a correct non-input may by smaller than (e.g., may be a third of) an increase in the score caused by a correct input 704. Alternatively or in addition, a color and/or an audio signal of the feedback for a correct input and a correct non-input may differ (e.g., a correct non-input may comprise a circle of a darker shade than a circle indicative of a correct input). By the difference in the increase of the score and/or by the difference in the visual and/or audible feedback between the correct input and the correct non-input, creating attentional bias on NoGo trials (e.g., correct non-inputs) may be avoided.

FIG. 8 shows an exemplary time line 708 for one repetition of performing the method steps 432, 434, 436 and 438 of the second task.

In the following, modifications to the performance metrics and the difficulty levels for the first task and for the second task will be described in connection with FIGS. 9 to 12.

In the first task (GNG), after a predefined number (e.g., five or six) of correct inputs and/or correct non-inputs (also denoted as "successful trials" and/or "correct trials") as represented by the difficulty level 902, the time limit for a Go response to be considered as correct (e.g., the RTT at reference sign 904 in FIG. 9) decreases.

In the second task (CAT), after a predetermined number (e.g. three) successful Go trials as represented by the difficulty level 902, the delay between the Go cue and the rendering of the physical object (e.g., the GSD with at reference sign 1004 in FIG. 10 the difference of the second time period and the GSD exemplified in seconds) decreases.

Exemplary parameters of an embodiment for reducing the RRT for the first task and the second task are displayed in Table 3.

TABLE 3

Difficulty parameters at each level for all tasks (in seconds)

| Level | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| GNG (RTT) | 1.1 | 1 | .9 | .8 | .725 | .675 | .625 | .575 | .55 | .525 | .5 | .475 | .4525 | .43 | .407 | .387 | .36 | .33 |
| CAT (1.25-GSD) | 0.88 | .81 | .74 | .67 | .62 | .57 | .53 | .49 | .455 | .42 | .39 | .36 | .335 | .31 | .29 | .27 | .26 | .25 |

By increasing the time pressure for receiving input in the step 424 of the first task and/or the step 436 of the second task, the task difficulty increases. Each input increases the probability to commit a speed error ("too late") and/or to commit an error to a NoGo trial (e.g., because a response prepotency increases). The 18 levels of task difficulty of the exemplary embodiment in Table 3 span from low time pressure ("very easy", e.g., at level 1) to an impossible time pressure corresponding to the minimal physiological RTT ("very difficult", e.g., at level 18). Each increase in the difficulty level may be indicated by a specific visual and/or audible (e.g., audiovisual) alert.

Figure 11:
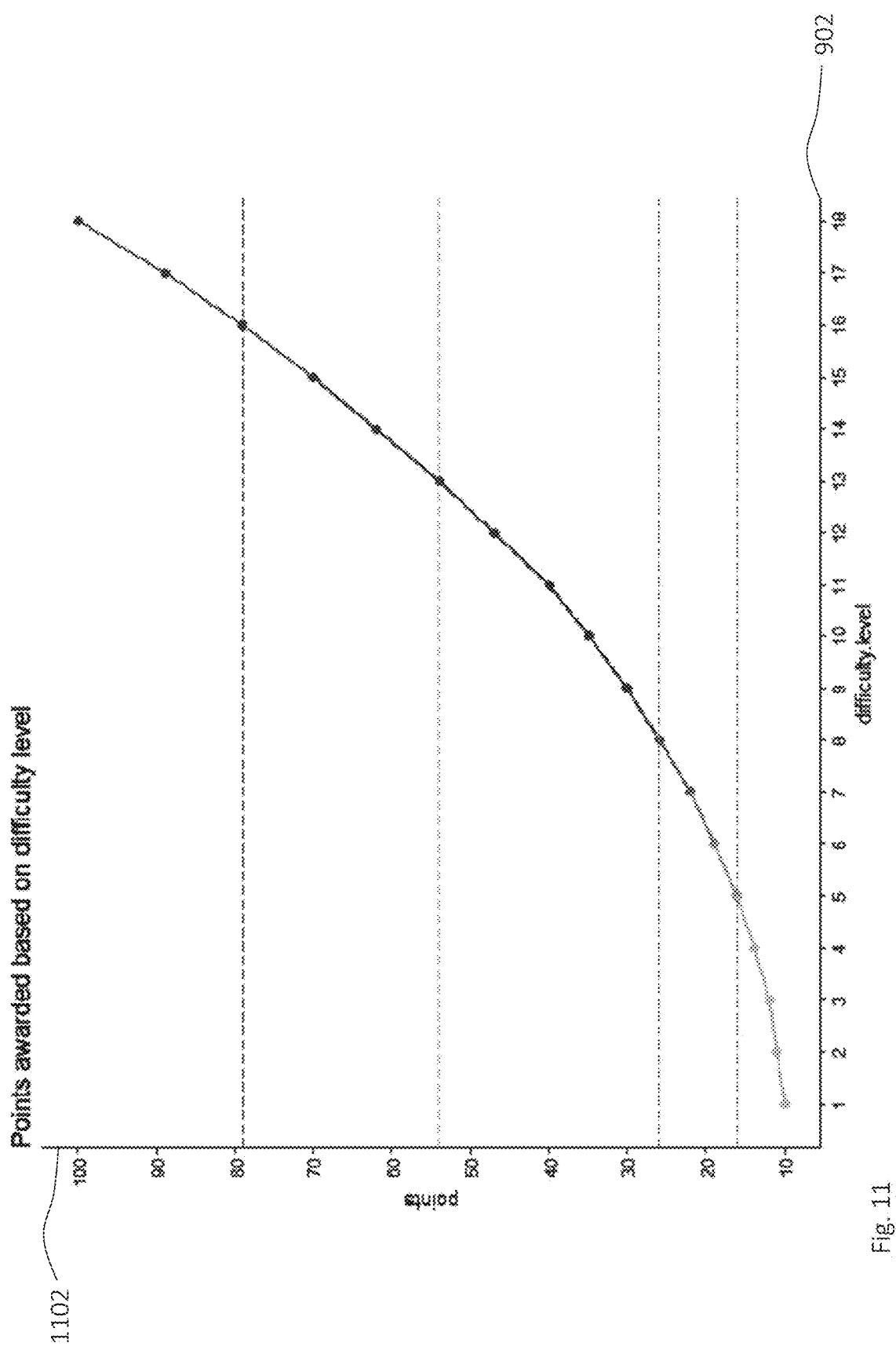
FIG. 11 shows an exemplary evolution of a score as a sub-sub-metric of the first sub-metric of any of the first and second metric as a function of a difficulty level.

The score (e.g., within the first sub-metric of the respective metric of the respective task) awarded for a correct trial may be increased with the difficulty level 902 as shown at reference sign 1102 in FIG. 11. Alternatively, the score may be increased by a multiplicative factor, e.g., as displayed in FIG. 12 at reference sign 1208.

A limited number of errors may be allowed per "run" and/or "session", as indicated by both a "speed" and an "accuracy" gauge with, e.g., a predetermined maximum of five levels each. If the user responds too late to a Go trial, the "speed" gauge is decreased one level. Alternatively or in addition, the user responds to a NoGo trial or does not respond to a Go trial, the "accuracy" gauge is decreased one level. These two 'life' gauges system (e.g., comprising an "accuracy" and a "speed" gauge) may be implemented to induce the user to remain in a stable speed-accuracy trade-off for repeatedly performing the steps of the first task and/or the second task. As soon as one of the two gauges reaches its predetermined minimum (also denoted as "empty"), the "run" and/or "session" is over. At the end of the "run" and/or "session", a score screen may appear informing the user about his/her increase in the first sub-metric of the respective metric of the respective task. Alternatively or in addition, the user's "local" ranking (e.g., how well he/she performed based on his/her own previous scores) may be displayed. If the last score was the user's best score, and/or if he/she reached his/her highest difficulty level, a rewarding alert may be played.

Figure 12:
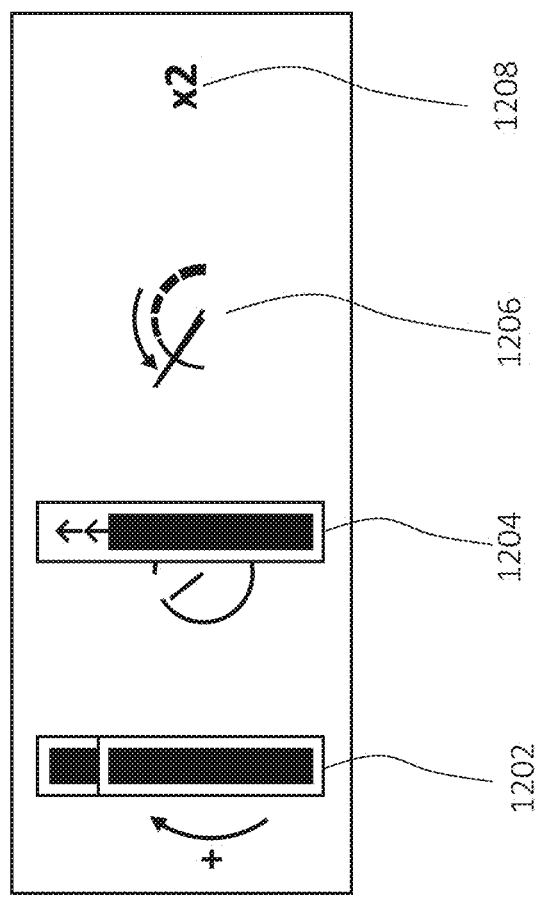
FIG. 12 shows a variety of exemplary possibilities for modifying a gauge (as a sub-sub-metric) of the second sub-metric and/or of decreasing a difficulty level and/or multiplying a score (as a sub-sub-metric) for the first sub-metric of the metric of one task such as by decreasing a score as a sub-sub-metric of the first sub-metric of the matric of the other task according to the cross-connections of the tasks in FIG. 4A.

The score (as a sub-sub-metric of the first sub-metric of the respective metric of the respective task) may be used for modifying (also denoted as "power-up") at least one sub-metric of the metric of the other task as displayed in FIG. 12.

For example, by reducing the score of one task by a predetermined amount, at least one of the gauges (as sub-sub-metrics of the second sub-metric) of the other task may be modified. At reference sign 1202, the predetermined maximum of the at least one gauge may be increased by a predetermined amount (e.g., depending on the score of the one task and/or a difficulty level of the other task, to which the gauge is associated). Alternatively or in addition, at reference sign 1204, the at least one gauge may be refilled periodically (e.g., every ten or twenty seconds within a "run" and/or "session") by a predetermined amount (e.g., by two supplementary levels) for a predefined time. Further alternatively or in addition, at reference sign 1206, the difficulty level (as a sub-sub-metric of the first sub-metric) may be decreased (e.g., by two levels for the remaining day and/or run and/or session). Still further alternatively or in addition, at reference sign 1208, a score of one task may be decreased in order to, e.g., temporarily, increase (e.g., multiply by a factor of two) a score (as a sub-sub-metric of the first sub-metric) awarded within the other task.

The score from one task may be reduced to modify at least one of the gauges 1202, 1204, the difficulty level 106 and/or the value 1208 of increasing the score of the other task. By this interconnection of the two tasks (e.g., displayed at reference signs 408, 410 in FIG. 4A), the efficacy of both the first task and the second task may be increased.

A "global" ranking table (e.g., comprising the user's best scores compared to the best scores of other users) may be accessed from the start menu. For example, the external controller 302 may provide the "global" ranking table stored by the storage server 306. Fake high and low scores may optionally be implemented in a database (e.g., comprising the best scores of all users and/or all HMIs) to motivate the users while avoiding discouraging the less successful ones.

The daily requirement of time for repeatedly performing the steps of each task may be represented by gauges in a level selection screen. One gauge (e.g., comprising the maximum of the gauge) may correspond to ten (10) minutes of time of repeatedly performing the steps of the task. After each run and/or session, the corresponding gauge may increase based on the amount of repeatedly performed steps and/or on the time before a run and/or session is terminated (e.g., due to an empty "accuracy" and/or "speed" gauge). Once the gauge for a given day is full and/or reaches its maximum, the user is expected to stop his/her daily repetitions of the given task. To complete the controlling of the HMI, a predefined level (e.g., a maximum of twenty) of gauges for each task in four weeks is required to be filled (e.g., comprising a total of four hundred, 400, minutes of controlling the HMI for the first task and for the second task).

The effectiveness of controlling the HMI may be reinforced by intrinsic motivation. Clear intrinsic and social challenging goals with progressive difficulty levels and a feedback on a user's ranking against his/her own and other users' scores may be employed. The social comparison may increase the perception of the reward for the user and increases the importance of increasing the score (e.g., by successful trials in each task). The user can take a rest by switching among the first task and the second task and by varying his/her overall experience, thereby preventing the user to stop controlling the HMI because of boredom or frustration. Alternatively or in addition, increasing scores can motivate the user to perform better (e.g., in terms of an increased number of successful trials) and to allow him/her to reiterate the same experience but with new task-specific configurations after modifying the respective metric ("power-ups"). The score of each of the first task and the second task can also create internal values. The scoring mechanisms can be strongly rewarding for the user because he/she can access additional contents after few hours of controlling the HMI. This possibility enables new actions that renew the HMI controlling experience and allows the user to develop new complex strategies after he/she has mastered the basic mechanics (e.g., the attention to a displayed physical object and/or rendered cue and/or an associated motoric response). Alternatively or in addition, an advantageous environment of controlling the HMI can create a rich and joyful experience for the user. Each step of the method 400 may have a specific (e.g., cinematic) visual design (e.g., to increase awareness and/or attention). Alternatively or in addition, an audio signal may be procedurally generated by mixing chunks (e.g., to help to avoid boredom and/or increase awareness and/or attention). Multiple sounds effects may support the overall experience and give direct feedbacks (e.g., specific to the task and/or a correctness of an input) to the user about his/her performance. From reward and punishment point of views, sound effects may be more and more pleasant by progressing in the tasks (e.g., throughout a run, session and/or day, and or with the total time spent on a task, for example measured by the number of days the HMI has already been controlled) and/or shame the user for an error. Alternatively or in addition, visual signals may judge the performance for each single step and/or run and/or session and/or at the end of controlling the HMI (e.g., from a first day to a final, ideal twentieth, day).

Figure 9:
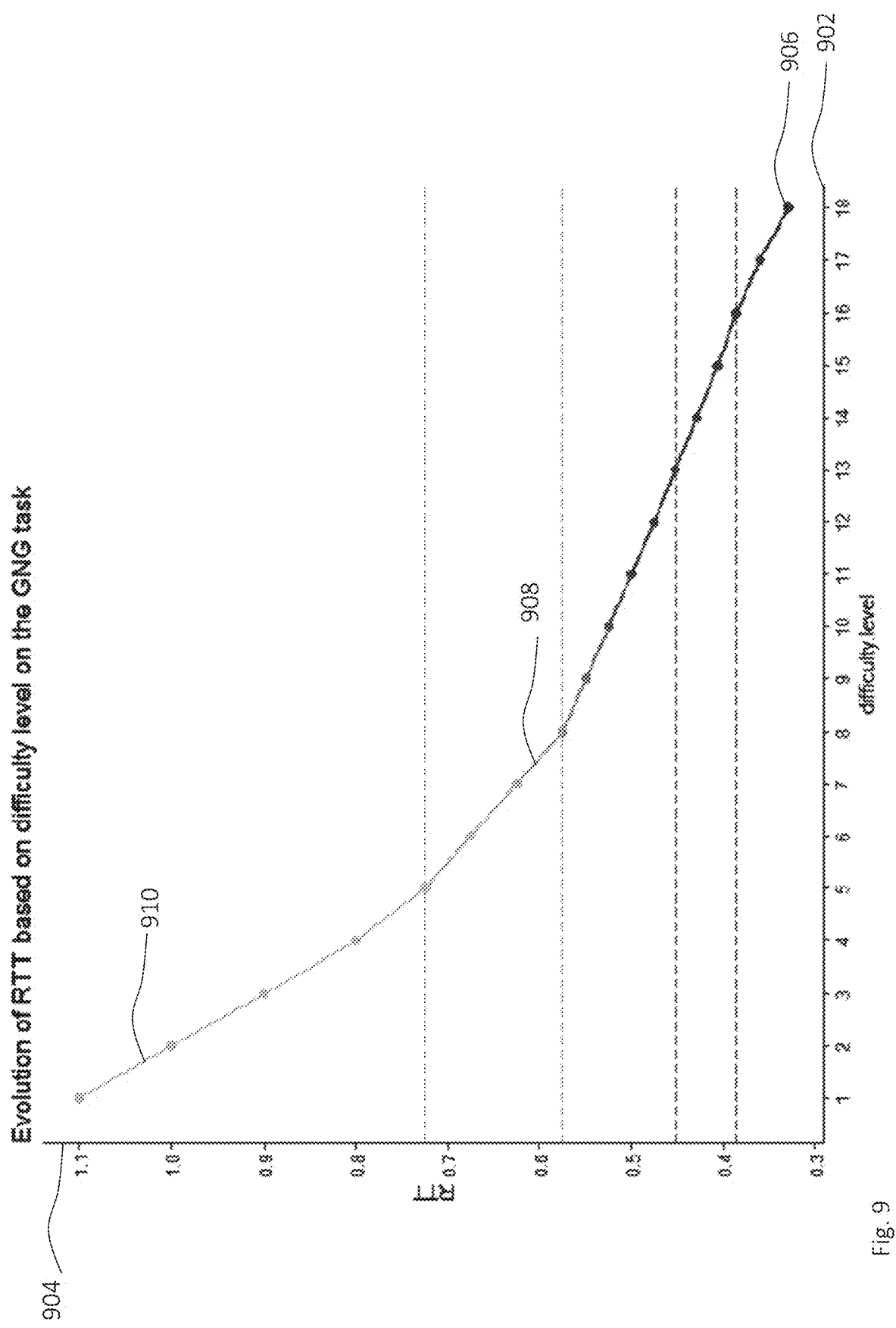
FIG. 9 shows an exemplary evolution of a Reaction Time Threshold (RTT) comprised in the predefined first time period for the first task as a function of a difficulty level.
Figure 10:
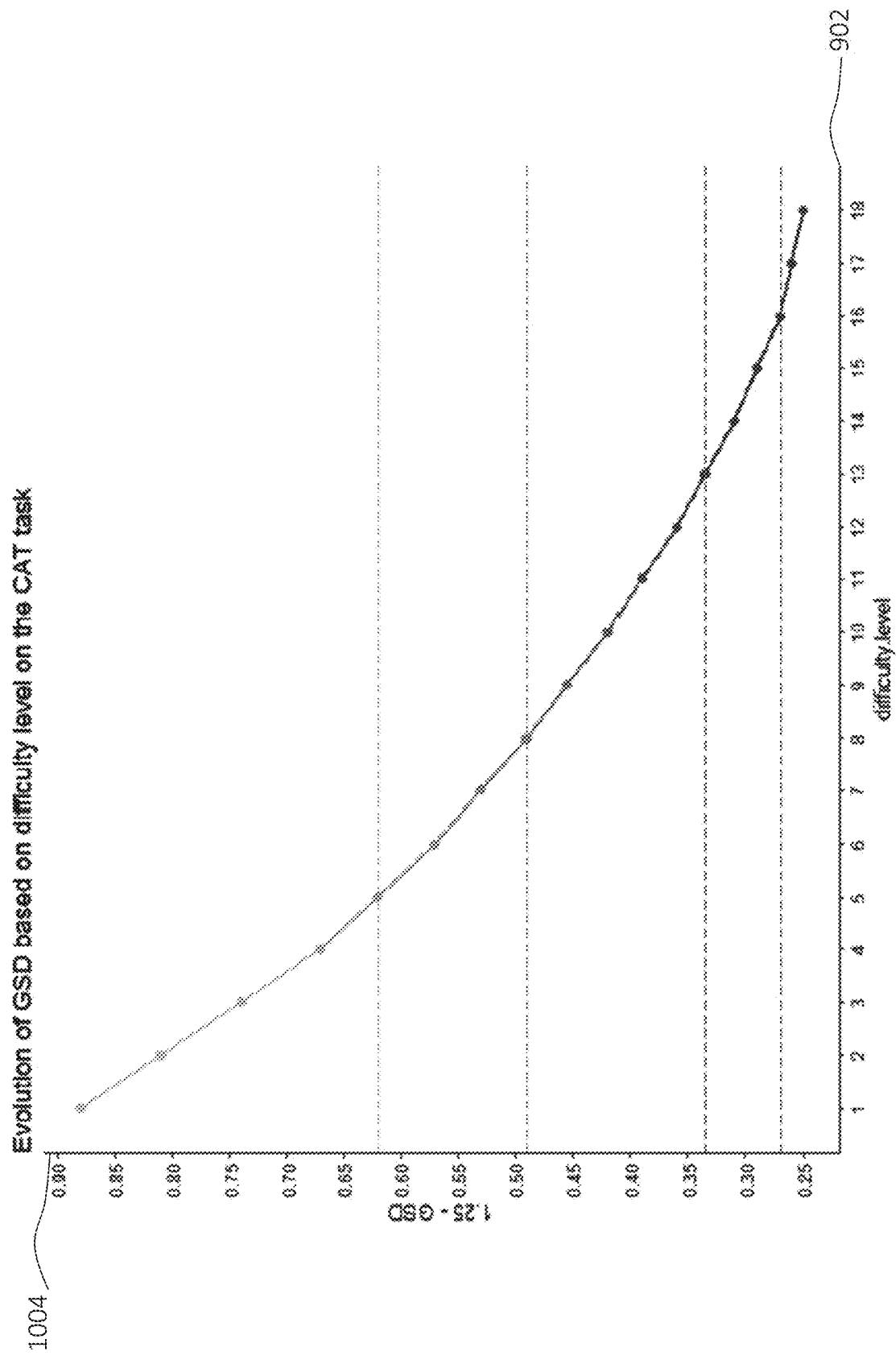
FIG. 10 shows an exemplary evolution of a Go Signal Delay (GSD) within the predefined second time period for the second task as a function of a difficulty level.

The decrease in the RRT, as exemplified in FIG. 9 for the first task, may follow a power function with a horizontal asymptote tending toward the fastest physiologically possible RTT 906. The feeling and/or perception of a difficulty by a user following such a curve may be at first flat and easy (e.g., for the RRTs at reference sign 910), then going progressively from mildly challenging (e.g., for RRTs around reference sign 908) to difficult levels of the RRT, until reaching a very challenging physiological level corresponding to the maxima of the physiologic capacity at reference sign 906.

The amount of increase in the first sub-metric (e.g. in the score as a sub-sub-metric) responsive to a correct trial may be adjusted to and/or increased with the difficulty level of the respective task. A multiplicative factor may be affixed to the score based on the difficulty level, following a curve similar to the opposite function of the difficulty progression curve, as exemplified in FIG. 11. The variable increase in the first sub-metric (e.g., in the score) can maximize the user's motivation with respect to the difficulty level. A user's motivation and/or engagement despite the difficulty being high may maintained and/or increased (e.g., with as a total time of controlling the HMI progresses).

An incomplete gesture (e.g., comprising a drag and drop of a physical object fulfilling the predefined criterion to a predefined position) for an input to the first task may be discouraged. E.g., an incomplete dragging may trigger a negative feedback indicating an error. By the (e.g., negative) feedback, an awareness and/or attention of the user of the HMI may be increased.

Maintaining a stable speed-accuracy trade-off may be ensured by a two-gauge system. When the user provides an input too late (also denoted as "speed error type") to a physical object fulfilling a predefined criterion in the first task and/or a cue being rendered in the second task a negative feedback (e.g., "too late") may be displayed. Alternatively or in addition, if the user provides an incorrect input and/or an incorrect non-input to a physical object in the first task and/or the second task (also denoted as "accuracy error type"), a negative feedback (e.g., "false" and/or a, typically colored such as in red, cross) may be displayed. The corresponding gauge may decrease, e.g., by a level. If at least one of the two gauges is emptied (e.g., the level reaches a predetermined minimum), the run and/or session is over. The "accuracy" and "speed" gauge system forces the user to focus on both speed and accuracy and thus avoid adopting an overly cautious or impulsive input strategy to improve his/her performance.

Feedbacks on comparison with previous own performances and/or performances by other users may be provided (e.g., with the external controller 302 and/or the storage server 306 in FIG. 3). E.g., the best performance of each user to each task may uploaded to the storage server 306 and used to give a rank to the user based on his/her past scores and/or based on other users' high-score. This form of social feedback can be strongly motivating.

The scores of one task may be used to acquire "power-ups" in the other task. By the "power-ups", a user's experience can be renewed. Alternatively or in addition, the "power-up" can facilitate getting a higher score without breaking the associative mechanisms of the task. Alternatively or in addition, to acquire a power-up to one task, the user needs to accumulate scores to the other task, rendering the tasks interconnected. By the interconnection of tasks, the user is forced to concentrate in both tasks. A good performance in his/her less-favorite task can help reaching a high-score in his/her favorite task. By the interconnection of tasks, an overall effectiveness of controlling the HMI can be increased.

The HMI may comprise a number of different counters. E.g., a counter may be dedicated to the time of a given task being performed per run, session and/or day. A further counter may, e.g., dedicated to counting the number of runs, sessions and/or days of controlling the HMI. Alternatively or in addition, the HMI may be configured to display a status of any one of the number of different counters. E.g., a remaining time per day and/or a number of remaining days for controlling the HMI for the first task and/or for the second task may be displayed.

As has become apparent from above description, embodiments of the technique allow for controlling of a HMI for a combination of a first task (GNG) and a second task (CAT). Controlling the HMI for the first task can reduce a value and/or a valuation of physical objects within one or more categories (e.g., unhealthy food items) by associating them with motoric inhibition.

Controlling the HMI for the second task can increase a value and/or a valuation of physical objects within one or more further categories (e.g., healthy food items) by biasing attention and approach tendency toward them. Alternatively or in addition, by performing both the first task and the second task, an assessment and/or unconscious bias of the physical objects can be synergistically modified, both towards predilictions of one or more categories and dislikes of one or more further categories.

Many advantages of the present disclosure will be fully understood from the foregoing description, and it will be apparent that various changes may be made in the form, construction and arrangement of the units and devices without departing from the scope of the disclosure and/or without sacrificing all of its advantages. Since the disclosure can be varied in many ways, it will be recognized that the disclosure should be limited only by the scope of the following claims.

It is understood that the foregoing description is that of the exemplary embodiments of the disclosure and that various changes and modifications may be made thereto without departing from the spirit and scope of the disclosure as defined in the appended claims.

What is claimed is:

1. A method of controlling a human machine interface (HMI), the method comprising:
    outputting, using the HMI, a predefined criterion applicable to each of a plurality of physical objects in a first task, wherein each of the plurality of physical objects is associated with a category within a group of at least two pairwise disjoint categories and the predefined criterion is fulfilled for each physical object associated with a first category within the group of categories and the predefined criterion is not fulfilled for each physical object associated with a second category within the group of categories,
    wherein the controlling of the HMI for the first task comprises repeatedly performing the steps of:
        rendering, using the HMI, a physical object out of the plurality of physical objects;
        monitoring the HMI for an input during a predefined first time period after the rendering of the physical object; and
        updating a first metric comprising a first sub-metric and a second sub-metric indicative of a performance measurement in the first task,
        wherein the first sub-metric of the first metric is increased if the input is received within the first time period and if the displayed physical object fulfills the predefined criterion,
        wherein the first sub-metric of the first metric is increased if the input is absent within the first time period and if the displayed physical object does not fulfill the predefined criterion,
        wherein the second sub-metric of the first metric is decreased if the input is received within the first time period and if the displayed physical object does not fulfill the predefined criterion, and
        wherein the second sub-metric of the first metric is decreased if the input is absent within the first time period and if the displayed physical object fulfills the predefined criterion; and
    rendering, using the HMI, a plurality of receptacles each enclosing one of the plurality of physical objects for a second task,
    wherein the controlling of the HMI for the second task comprises repeatedly performing the steps of:
        rendering a physical object out of the plurality of physical objects at any one of the receptacles for a predefined second time period;
        selectively rendering, using the HMI, a cue at the rendered physical object within the second time period;
        monitoring the HMI for an input responsive to the rendering of the physical object within the second time period; and
        updating a second metric comprising a first sub-metric and a second sub-metric indicative of a performance measurement in the second task, wherein the first sub-metric of the second metric is increased if the input is received within the second time period at the position of the selectively rendered cue, wherein the first sub-metric of the second metric is increased if the input is absent within the second time period and if no cue was selectively rendered, wherein the second sub-metric of the second metric is decreased if the input at the position of the physical object is received within the second time period and if no cue was selectively rendered, and wherein the second sub-metric of the second metric is decreased if the input is absent within the second time period and the cue was selectively rendered.

2. The method of claim 1, wherein the first task is repeated consecutively for a predefined third time period and/or wherein the second task is repeated consecutively for a predefined fourth time period, optionally wherein the third time period and the fourth time period have equal length.

3. The method of claim 1, wherein the predefined first time period and/or a time of rendering the cue within the predefined second time period decreases with at least one of a value of the first sub-metric of the respective metric indicative of the performance measurement of the respective task, a number of repetitions of the respective task and a number of performances of the method comprising repetitions of the first task and of the second task.

4. The method claim 1, wherein each of the second sub-metric of the first metric and the second sub-metric of the second metric corresponds to or is represented by at least one gauge, wherein each gauge comprises a predetermined maximum and a predetermined minimum, and wherein at each start of repeatedly controlling the HMI for the respective task, each of the at least one gauge of the respective task is filled or set to the predetermined maximum, and wherein the repeatedly controlling of the HMI for the respective task terminates if at least one of the at least one gauge of the respective task is emptied to or reaches the predetermined minimum.

5. The method of claim 4, wherein controlling the HMI for the first task further comprises the step of:

modifying at least one of the predetermined maximum and an initial state or filling of the at least one gauge corresponding to or representing the second sub-metric of the first metric before repeatedly controlling the HMI for the first task based on a value of the first sub-metric of the second metric; and wherein controlling the HMI for the second task further comprises the step of:

modifying at least one of the predetermined maximum and an initial state or filling of the at least one gauge corresponding to or representing the second sub-metric of the second metric before repeatedly controlling of the HMI for the second task based on a value of the first sub-metric of the first metric.

6. The method claim 1, wherein the at least one gauge corresponding to or representing the second sub-metric of the first metric comprises at least one of a gauge indicative of an accuracy of the input for the first task and a gauge indicative of the speed of the input for the first task, and/or wherein the at least one gauge corresponding to or representing the second sub-metric of the second metric comprises at least one of a gauge indicative of an accuracy of the input for the second task and a gauge indicative of the speed of the input for the second task.

7. The method of claim 1, further comprising a step of:

configuring the HMI by assembling the categories of the plurality of physical objects based on an initial configuration input for each of an extended plurality of physical objects comprising the plurality of physical objects.

8. The method of claim 7, further comprising the steps of:

receiving a final configuration input for each of the plurality of physical objects; and outputting a comparison of the initial configuration input and the final configuration input.

9. The method of claim 1, wherein the input comprises at least one of:

a gesture moving the physical object for the first task;

a physical contact with the rendered physical object for the second task; and a selection of a mark on a scale for the configuring of the HMI.

10. The method of claim 1, wherein the cue of the second task comprises an audiovisual signal.

11. The method of claim 1, wherein the HMI is in data communication with an external controller for reporting at least one of:

a tag indicative of the HMI and/or of a user of the HMI;

configuring the HMI;

a time indicative of controlling the HMI repeatedly for the first task and/or for the second task; and the updates of the first metric and of the second metric, and optionally wherein the external controller triggers a notification if the updates of the first metric and of the second metric deviate from a predefined schedule.

12. The method of claim 11, wherein the external controller is configured to provide a feedback to a user of the HMI responsive to the reported updates of the first metric and of the second metric.

13. A computer program product comprising program code portions for performing the steps of claim 1 when the computer program product is executed on one or more computing devices, optionally stored on a computer-readable recording medium.

14. A device for controlling a HMI, the device comprising the HMI and processing circuitry configured to perform the steps of claim 1.

15. A system for controlling a HMI, the system comprising at least one of:

a plurality of devices according to claim 14;

an external controller configured for data communication with each of the devices for receiving the updates of the first metric and the second metric and optionally for triggering a notification to any one of the devices; and a storage server configured to store the updates of the first metric and the second metric for each of the devices and for providing feedback to a user of each of the devices.

* * * * *